United States Patent [19]

Wallace et al.

[11] Patent Number: 4,879,226

[45] Date of Patent: Nov. 7, 1989

[54] NOVEL HUMAN PHYSIOLOGICALLY ACTIVE POLYPEPTIDE

[75] Inventors: Robert B. Wallace, West Covina, Calif.; Hirataka Itoh, Fuji, Japan

[73] Assignee: Asahi Kasei Kogyo Kabushiki Kaisha, Osaka, Japan

[21] Appl. No.: 597,372

[22] Filed: Apr. 6, 1984

[51] Int. Cl.[4] .................. C12P 21/00; C12N 15/00; C12N 1/20; C07H 15/12

[52] U.S. Cl. ................................ 435/68; 530/350; 530/351; 530/828; 435/252.33; 435/70; 435/172.3; 435/255; 435/320; 435/240.2; 435/948; 536/27; 514/2; 514/12; 514/21; 935/9; 935/11; 935/56; 935/73

[58] Field of Search ................ 514/2, 8, 12; 260/112 R, 112 B, 112.5 R; 435/68, 70, 172.3, 255, 317, 948, 320, 240.2, 240.4; 424/85; 536/27; 935/9, 11, 13, 27, 29, 56, 60, 73; 530/350, 351, 828

[56] References Cited

U.S. PATENT DOCUMENTS

| | | | |
|---|---|---|---|
| 4,309,418 | 1/1982 | Green | 514/21 |
| 4,359,415 | 11/1982 | Sloane | 530/395 |
| 4,447,355 | 5/1984 | Sakamoto et al. | 550/351 |
| 4,495,282 | 1/1985 | Ohnishi et al. | 530/331 |
| 4,529,594 | 7/1985 | Hayashi et al. | 530/351 |
| 4,711,842 | 12/1987 | Taniyama et al. | 435/68 |
| 4,777,241 | 10/1988 | Irikura et al. | 530/350 |
| 4,791,101 | 12/1988 | Adolf | 514/2 |

FOREIGN PATENT DOCUMENTS

| | | | |
|---|---|---|---|
| 29337/84 | 6/1984 | Australia | 435/68 |
| 36014/84 | 11/1984 | Australia | 435/68 |
| 0086475 | 8/1983 | European Pat. Off. | 435/68 |
| 0090892 | 10/1983 | European Pat. Off. | 433/68 |
| 0131789 | 1/1985 | European Pat. Off. | 435/68 |
| 58107197 | of 0000 | Japan | 435/68 |
| 57-140725 | 6/1982 | Japan | 435/68 |
| 59-01288 | 4/1984 | Japan | 435/68 |
| 2106117 | 4/1983 | United Kingdom | 435/68 |
| 2117385 | 10/1983 | United Kingdom | 435/68 |

OTHER PUBLICATIONS

*Molecular Biology of the Gene* 3rd Edition James Watson published by W. A. Benjamin, Inc., 1977 "Polypeptride".

Broxmeyer et al. *J. Immunol.* vol. 136 (12) pp. 4487–4495, Jun. 15, 1986.

Carswell et al. *Proc. Natl. Acad Sci.* vol. 72, (9) pp. 3666–3670 Spt. 1975.

Rubin et al *Proc. Natl. Acd. Sci.*, vol. 82, pp. 6637–6641, Oct. 1985.

*International Dictionary of Med.* and Biol., vol. II published by John Wiley & Sons "Lectin".

*Methods in Enzymol* vol. 70, Part A "Immunological Techniques" Edited by Helen Van Vunakis et al. 1980.

Merck Index 10th Edition 1983 "Lectin".

Lymphokines, vol. 2, edited by E. Pick, Academic Press, N.Y., 235–272 (1980).

Mannel et al., Daniela N., Infect. Immun., 30, 523–530 (1980).

Haranaka et al, Katsuyuki, Japan J. Exp. Med., 51, 191–194 (1981).

Helson et al., L., Expl. Cell Biol., 47, 53–60 (1979).

Green et al, Saul, Proc. Nat. Acad. Sci. U.S.A., 73, 381–385 (1976).

Matthews et al, N., Br. J. Cancer, 38, 202–309 (1978).

Mannel et al., Daniela N., J. Immun., 124, 1106–1110 (1980).

Oettgen et al., H. F., Recent Results in Cancer Res., No. 75, 207–212 (1980).

(List continued on next page.)

*Primary Examiner*—Robin L. Teskin
*Attorney, Agent, or Firm*—Birch, Stewart, Kolasch & Birch

[57] ABSTRACT

A human physiologically active polypeptide, human Tumor Necrosis Factor (human TNF), comprising a specific amino acid sequence of 155 amino acid residues. The base sequence of the DNA coding for the human TNF has been determined using rabbit TNF cDNA. The human TNF can be advantageously produced on a large scale by recombinant DNA technique. The human TNF of the present invention has been found to be excellent in inducing necrosis of tumors with no toxic effect upon the normal tissues of the living body.

40 Claims, 7 Drawing Sheets

OTHER PUBLICATIONS

Kull et al., Frederick C., J. Immun., 126, 1279–1283 (1981).
Interleukins, Lymphokines and Cytokines, edited by J. J. Oppenheim and Stanley Cohen, Academic Press, Inc., 5211–526 (1983).
Matthews, N., Immunology, 48, 321–327 (1983).
Carswell et al, E. A., Proc. Nat. Acad. Sci. USA, 72 (9) 3666–3670 (1975).
Ruff et al., Michael R., J. Immunol., 125 (4), 1671–1677 (1980).
Matthews et al., N., Br. J. Cancer, 42, 416–422 (1980).
Reed et al., William P., J. Immunol., 115, 395 (1975).
Matthews et al., N., Immunology, 44, 135 (1981).
Williamson et al., Barbara D., Proc. Nat. Acad. Sci. USA, 80, 5397 (1983).
Matthews, N., Br. J. Cancer, 44 (3), 419–424 (1981).
Nissen-Meyer et al, Jon, Infection and Immunity, 38, 67–73 (1982).
Aggarwal et al., J. Biol. Chem., 259, 686–691 (Jan. 1984).
Aggarwal et al., J. Biol. Chem., 260, 2345–2354 (Feb. 1985).
Cerletti et al., Lymphokine Research, vol. 6, No. 1 (Jan. 1987).
Gray et al., Nature, 312, 721–724 (Dec. 1984).
Kelker et al., Int. J. Cancer, 36, 69–73 (1985).
Marmenout, Eur. J. Biochem., 152, 515–522 (1985).
Nikkei Biotech, p. 3, left column, lines 8 to 2 from the bottom (Feb. 25, 1985).
Nikkei Biotech, p. 10, right column, line 9 from the bottom to p. 11, left column, line 5 (Mar. 11, 1985).
Pennica et al., Nature, 312, 724–727 (Dec. 1984).
Rubin et al., J. Exp. Med., 164, 1350–1355 (Oct. 1985).
Shirai et al., Nature, 313, 803–806 (Feb. 1985).
Ruff et al., Chem. Abstracts, vol. 95, No. 113062b (1981).
Matthews, et al, Chem. Abstracts, vol. 94, No. 78873x (1981).
Hammerstroem et al., Chem. Ab., 92:158695g (1980).
Hammerstroem et al., Chem. AB., 92:196005x (1980).
Mannel et al, Chem. Ab., 93:231791v (1980).

NOVEL HUMAN PHYSIOLOGICALLY ACTIVE POLYPEPTIDE

This invention relates to a deoxyribonucleic acid (hereinafter referred to as "DNA") coding for a novel human physiologically active polypeptide. This invention also relates to a replicable recombinant DNA containing the DNA, a microorganism or cell transformed with the replicable recombinant DNA, a novel human physiologically active polypeptide obtained by expressing the DNA, a substantially pure human physiologically active polypeptide having the amino acid sequence described herein, pharmaceutical compositions containing the physiologically active polypeptide as the effective ingredient, and a process for producing the human physiologically active polypeptide. More particularly, the present invention is concerned with a DNA coding for human TNF (Tumor Necrosis Factor), human TNF having an amino acid sequence deduced from the base sequence of the DNA, a process for producing human TNF from the DNA utilizing recombinant DNA technology, and the use of the product obtained by the process.

In the present specification, amino acids and peptides are represented using abbreviations, as indicated below, approved by IUPAC-IUB Commission on Biochemical Nomenclature (CBN). Incidentally, with respect to amino acids and the like having isomers, those represented by the following abbreviations are of the L-configuration unless otherwise specified.

Gln: glutamine residue
Asp: aspartic acid residue
Pro: proline residue
Tyr: tyrosine residue
Val: valine residue
Lys: lysine residue
Glu: glutamic acid residue
Ala: alanine residue
Asn: asparagine residue
Leu: leucine residue
Phe: phenylalanine residue
Gly: glycine residue
His: histidine residue
Ser: serine residue
Thr: threonine residue
Ile: isoleucine residue
Trp: tryptophan residue
Arg: arginine residue
Met: methionine residue
Cys: cysteine residue Polydeoxyribonucleotides and oligodeoxyribonucleotides are represented by sequences of deoxynucleotide residues which are abbreviated as follows:

A: 2'-deoxyadenylic acid residue
C: 2'-deoxycytidylic acid residue
G: 2'-deoxyguanylic acid residue
T: thymidylic acid residue Unless otherwise specified, the left end of the sequence of deoxynucleotides is the 5' end.

There are known various substances having a capacity for stimulating the reticuloendothelial system, for example, physiologically active substances having anti-tumor activity which are induced by various Gram-positive bacteria and endotoxins. Specifically, Carswell et al discovered that the serum from CD-1 Swiss mice infected with bacillus Calmette-Guerin (BCG), and after two weeks, followed by intravenous injection of endotoxin has cytotoxic activity against cultured L cells and also discovered a phenomenon that it induces hemorrhagic necrosis of transplanted Meth A sarcoma in the $(BALB/c \times C57BL/6)F_1$ mouse. They gave the name of TNF (Tumor Necrosis Factor) to the active substance in the serum [Proc. Nat. Acad. Sci. USA, Vol. 72 (No. 9), pp. 3666–3670 (1975)]. Thereafter, Ruff et al reported that the rabbit TNF prepared according to the above-mentioned method proposed by Carswell et at was purified about 2,000-fold over serum (J. Immunol., Vol. 125 (No. 4), pp. 1671–1677 (1980)]. Further, Matthews et al reported that the rabbit TNF was purified about 1,000-fold over the serum [Br. J. Cancer, Vol. 42, pp. 416–422 (1980)]. However, in Ruff et al and Matthews et al, the tumor necrosis effect with respect to the purified TNF is not confirmed in animal experiments.

Japanese Patent Application Laid-Open Specification No. 57-140725 (1982) discloses a process for isolating and purifying a proteinaceous physiologically active substance having anti-tumor activity, which is induced by administering to a mammal such as mouse, rabbit or guinea pig at least one substance having a capacity for stimulating the reticuloendothelial system and then injecting endotoxin from a Gram-negative bacterium into the mammal, or by adding endotoxin from a Gram-negative bacterium to a tissue culture containing activated macrophages from a mammal. In this Japanese Patent Application Laid-Open Specification, there are also disclosed the molecular weight and isoelectric point of the purified proteinaceous physiologically active substance (molecular weight, $39,000 \pm 5,000$ as measured by gel filtration and SDS-polyacrylamide gel electrophoresis; isoelectric point, pH $3.9 \pm 0.3$ as measured by isoelectric focusing) but not any detailed structure of the proteinaceous physiologically active substance.

Meanwhile, Matthews reported that there is obtained a substance having cytotoxic activity against L cells by a process in which BCG is injected into a rabbit and mononuclear phagocytes from various tissues of the rabbit are obtained two weeks after the injection, followed by addition of endotoxin to the cell culture of the mononuclear phagocytes [Br. J. Cancer, Vol. 44 (3), pp. 418–424 (1981)]. However, in his report, the detailed structure of the obtained substance is not disclosed and, further, there is no evidence showing that the obtained substance is identical with TNF found in the serum.

Further, there are a number of printed publications reporting that factors having TNF-like bioactivity or a bioactivity similar to that of TNF. For example, Reed et al found such a factor in macrophages and the like present in human peripheral blood [J. Immunology, Vol. 115, p. 395 (1975)], Matthews et al in leukemia cells derived from human peripheral blood monocytes or from a patient suffering from myelogenous monocytic leukemia [Immunology, Vol. 44, p. 135 (1981)], Williamson et al in human B cells transformed with Epstein-barr virus [Proc. Nat. Acad. Sci. USA, Vol. 80, p. 5397 (1983)], and Aggarwal et al in lymphoblastoid 1788 cell line. "Purification and Characterization of Lymphotoxin from Human Lymphoblastoid Cell Line 1788", pp. 521–525, Interleukins, Lymphokines and Cytokines, Academic Press (1983). The above-mentioned factors are also disclosed in Japanese Patent Application Laid-Open Specifications Nos. 58-15921 (1983), 58-21621 (1983), 58-107197 (1983) and 58-225024 (1983), and British Patent Application Laid-Open Specifications Nos. 2,106,117 and 2,117,385. However, the cells or cell lines capable of efficiently producing such factors have not yet been found. Further, with respect to such factors, there are many matters to be elucidated such as their structures and properties.

Ito [Japanese Patent Application No. 58-251817 (1983)] made studies on properties and structure of rabbit TNF and rabbit-TNF producing cells. As a result, he obtained cells capable of producing a substance having cytotoxic activity against L cells by administering a substance having a capacity for stimulating the reticuloendothelial system to a rabbit, followed by injection of endotoxin derived from a bacterium into the rabbit, and then obtained such a substance using those cells. He also affirmed that the molecular weight and immunological properties of the substance having cytotoxic activity against L cells obtained using the above obtained cells are in agreement with those of TNF obtained from rabbit serum. Meanwhile, with the progress of genetic manipulation techniques, it became possible to determine the structure of a protein so long as a DNA coding for the protein is obtained in isolated form. This is so because the structure of the isolated DNA can be determined and, then, the structure of the protein can be deduced from the structure of the DNA. Further, it became possible to produce a protein from a DNA coding for the protein utilizing a microorganism or cell culture. Ito applied the above-mentioned genetic manipulation techniques to the cells capable of producing a substance having cytotoxic activity against L cells. As a result, he succeeded in isolating a DNA coding for rabbit TNF, determining the structures of the DNA and rabbit TNF, and producing rabbit TNF using the DNA.

As is apparent from the foregoing, Ito has made a great success in producing rabbit TNF. However, it should be noted that the administration of TNF to an animal which is not the origin of the TNF has a danger that anaphylactic shock might be caused. This is so because TNF is a polypeptide and, hence, when TNF is administered to an animal which is not the origin of the TNF, the TNF functions as an antigen to produce an antibody. For this reason, when TNF is intended to be administered to a human body, the use of TNF derived from human beings is highly preferable. However, even the structure of human TNF has not been successfully elucidated. Therefore, the determination of the structure of the DNA coding for human TNF has been strongly needed.

The present inventors have made extensive and intensive studies on the structure of the DNA coding for human TNF. As a result, the present inventors have surprisingly found that a human polypeptide gene and a rabbit TNF gene can be cloned by the use of rabbit cDNA as a probe, that the DNA coding for human polypeptide can be skillfully isolated and the structure thereof can be determined by comparison between rabbit TNF gene, human polypeptide gene and rabbit cDNA with respect to the homology of their base sequences, that the structure of pure DNA coding for human polypeptide can be skillfully determined and such a pure DNA can be obtained, and that a human polypeptide produced using the DNA coding for the human polypeptide has a cytotoxic activity against L cells.

The present invention has been made based on such novel findings.

Therefore, it is an object of the present invention to provide a human physiologically active polypeptide.

It is another object of the present invention to provide a DNA coding for human TNF.

It is still another object of the present invention to provide a replicable recombinant DNA comprising a DNA coding for human TNF and a replicable expression vehicle.

It is a further object of the present invention to provide a microorganism or a cell transformed with a recombinant DNA of the kind as mentioned above.

It is a further object of the present invention to provide a process for producing a human physiologically active polypeptide of the kind as mentioned above.

The foregoing and other objects, features and advantages of the present invention will be apparent from the following detailed description taken in connection with the accompanying drawings in which.

Figure 1:
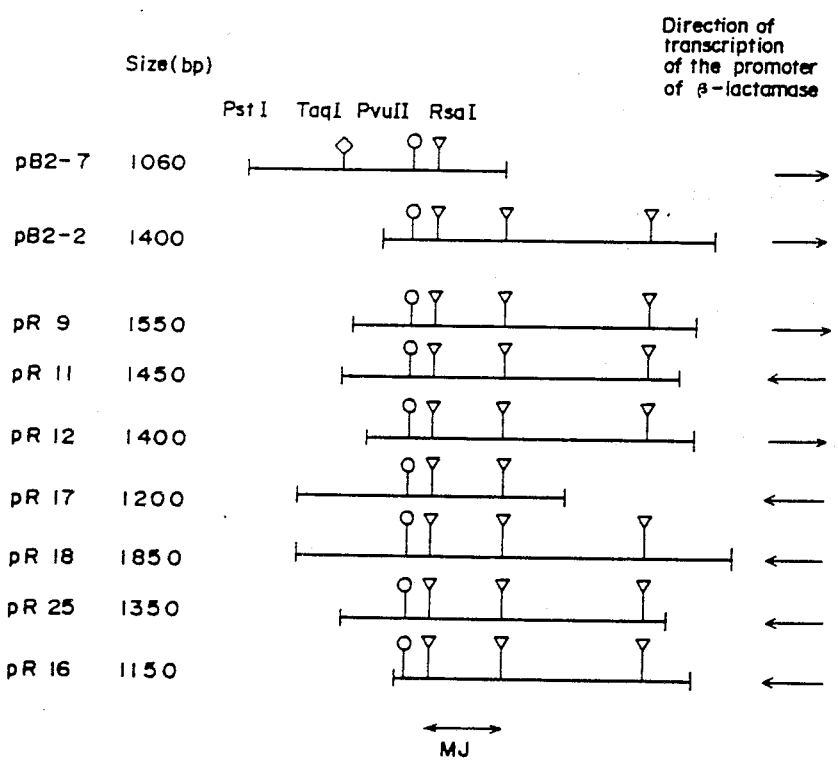
FIG. 1 illustrates the restriction maps of plasmid inserts each containing a DNA coding for a conventional rabbit physiologically active polypeptide.

Essentially, according to the present invention, there is provided a human physiologically active polypeptide having an amino acid sequence represented by the following formula (I):

Ser Ser Ser Arg Thr Pro Ser Asp Lys Pro Val Ala His
Val Val Ala Asn Pro Gln Ala Glu Gly Gln Leu Gln
Trp Leu Asn Arg Arg Ala Asn Ala Leu Leu Ala Asn
Gly Val Glu Leu Arg Asp Asn Gln Leu Val Val Pro
Ser Glu Gly Leu Tyr Leu Ile Tyr Ser Gln Val Leu Phe
Lys Gly Gln Gly Cys Pro Ser Thr His Val Leu Leu Thr
His Thr Ile Ser Arg Ile Ala Val Ser Tyr Gln Thr Lys
Val Asn Leu Leu Ser Ala Ile Lys Ser Pro Cys Gln Arg
Glu Thr Pro Glu Gly Ala Glu Ala Lys Pro Trp Tyr
Glu Pro Ile Tyr Leu Gly Gly Val Phe Gln Leu Glu Lys
Gly Asp Arg Leu Ser Ala Glu Ile Asn Arg Pro Asp Tyr
Leu Asp Phe Ala Glu Ser Gly Gln Val Tyr Phe Gly Ile
Ile Ala Leu wherein Gln stands for a glutamine residue, Asp an aspartic acid residue, Pro a proline residue, Tyr a tyrosine residue, Val a valine residue, Lys a lysine residue, Glu a glutamic acid residue, Ala an alanine residue, Asn an asparagine residue, Leu a leucine residue, Phe a phenylalanine residue, Gly a glycine residue, His a histidine residue, Ser a serine residue, Thr a threonine residue, Ile an isoleucine residue, Trp a tryptophan residue, Arg an arginine residue, Met a methionine residue, and Cys a cysteine residue.

The human physiologically active polypeptide of the present invention also includes a polypeptide having an amino acid methionine attached to the N-terminus of the above-mentioned amino acid sequence and an intermediate having a partial or entire signal peptide for human TNF attached to the N-terminus of the above-mentioned amino acid sequence. It is possible to change part of the structure of a DNA coding for a polypeptide by natural or artificial mutation without significant change of the activity of the polypeptide. The human physiologically active polypeptide of the present invention includes a polypeptide having a structure corresponding to homologous variant(s) of the polypeptide having the above-mentioned amino acid sequence. All such physiologically active polypeptides are hereinafter referred to as "human TNF".

In another aspect of the present invention, there is provided a deoxyribonucleic acid comprising a base sequence coding for a human physiologically active polypeptide, said human physiologically active polypeptide having an amino acid sequence represented by the following formula (I):

Ser Ser Ser Arg Thr Pro Ser Asp Lys Pro Val Ala His Val Val Ala Asn Pro Gln Ala Glu Gly Gln Leu Gln Trp Leu Asn Arg Arg Ala Asn Ala Leu Leu Ala Asn Gly Val Glu Leu Arg Asp Asn Gln Leu Val Val Pro Ser Glu Gly Leu Try Leu Ile Tyr Ser Gln Val Leu Phe Lys Gly Gln Gly Cys Pro Ser Thr His Val Leu Leu Thr His Thr Ile Ser Arg Ile Ala Val Ser Tyr Gln Thr Lys Val Asn Leu Leu Ser Ala Ile Lys Ser Pro Cys Gln Arg Glu Thr Pro Glu Gly Ala Glu Ala Lys Pro Trp Tyr Glu Pro Ile Tyr Leu Gly Gly Val Phe Gln Leu Glu Lys Gly Asp Arg Leu Ser Ala Glu Ile Asn Arg Pro Asp Tyr Leu Asp Phe Ala Glu Ser Gly Gln Val Tyr Phe Gly Ile Ile Ala Leu wherein Gln stands for a glutamine residue, Asp an aspartic acid residue, Pro a proline residue, Tyr a tyrosine residue, Val a valine residue, Lys a lysine residue, Glu a glutamic acid residue, Ala an alanine residue, Asn an asparagine residue, Leu a leucine residue, Phe a phenylalanine residue, Gly a glycine residue, His a histidine residue, Ser a serine residue, Thr a threonine residue, Ile an isoleucine residue, Trp a tryptophan residue, Arg an arginine residue, Met a methionine residue, and Cys a cysteine residue.

In further aspect of the present invention, there is provided a deoxyribonucleic acid comprising at least one base sequence selected from the group consisting of a base sequence represented by the following formula (II) and a complementary base sequence to said base sequence:

TCA TCT TCT CGA ACC CCG AGT GAC AAG
CCT GTA GCC CAT GTT GTA GCA AAC CCT
CAA GCT GAG GGG CAG CTC CAG TGG CTG
AAC CGC CGG GCC AAT GCC CTC CTG GCC
AAT GGC GTG GAG CTG AGA GAT AAC CAG
CTG GTG GTG CCA TCA GAG GGC CTG TAC
CTC ATC TAC TCC CAG GTC CTC TTC AAG
GGC CAA GGC TGC CCC TCC ACC CAT GTG
CTC CTC ACC CAC ACC ATC AGC CGC ATC
GCC GTC TCC TAC CAG ACC AAG GTC AAC
CTC CTC TCT GCC ATC AAG AGC CCC TGC
CAG AGG GAG ACC CCA GAG GGG GCT GAG
GCC AAG CCC TGG TAT GAG CCC ATC TAT
CTG GGA GGG GTC TTC CAG CTG GAG AAG
GGT GAC CGA CTC AGC GCT GAG ATC AAT
CGG CCC GAC TAT CTC GAC TTT GCC GAG
TCT GGG CAG GTC TAC TTT GGG ATC ATT
GCC CTG

Wherein A stands for a deoxyadenylic acid residue, G a deoxyguanylic acid residue, C a deoxycytidylic acid residue and T thymidylic acid residue and wherein the left end and right end of the formula (II) represent 5'-hydroxyl group side and 3'-hydroxyl group side, respectively.

The DNA of the present invention includes a DNA comprising a base sequence having ATG (A, T and G are as mentioned above) attached to the 5'-end of the above-mentioned base sequence in order to produce mature human TNF by means of culture of a microorganism or cell. The DNA of the present invention also includes a DNA having a 5'-flanking DNA coding for a partial or entire signal peptide of human TNF.

The structure of a DNA and the structure of the polypeptide deduced therefrom may be partially changed by natural or artificial mutation without casing the main activity of the polypeptide to be changed. Hence, the DNA of the present invention may alternatively have a base sequence that codes for a polypeptide with a structure corresponding to that of a homologous variant of any of the aforementioned polypeptides.

In accordance with degeneracy of genetic code, it is possible to substitute at least one base of the base sequence of a gene by another kind of base without causing the amino acid sequence of the polypeptide produced from the gene to be changed. Hence, the DNA of the present invention may also have any base sequence that has been changed by substitution in accordance with degeneracy of genetic code. In this instance, the amino acid sequence deduced from the base sequence obtained by the above-mentioned substitution is identical with the amino acid sequence of the formula (I) as defined before.

In a further aspect of the present invention, there is provided a replicable recombinant DNA which comprises the above-mentioned deoxyribonucleic acid according to the present invention and a replicable expression vehicle. The recombinant DNA is capable, in a transformed microorganism or cell culture, of expressing a polypeptide comprising the amino acid sequence of human TNF. As the suitable vehicle, there may be mentioned, for example, pHTNF-lacUV5-1 and pHTNF-lacUV5-2 expression vehicle.

Further, the present invention is directed to a microorganism or cell culture transformed with a recombinant DNA capable of expressing a polypeptide comprising the amino acid sequence of human TNF. Examples of such microorganism or cell culture include *Escherichia coli*, *Bacillus subtilis*, yeasts and higher animal cells.

In an even further aspect of the present invention, there is provided a method for producing the human physiologically active polypeptide of the present invention which comprises:

(a) ligating the deoxyribonucleic acid of the formula (II) as defined above to a replicable expression vehicle to obtain a replicable recombinant DNA comprising said deoxyribonucleic acid and said replicable expression vehicle;

(b) transforming cells of a microorganism or cell culture with said replicable recombinant DNA to form transformants;

(c) selecting said transformants from parent cells of the microorganism or cell culture;

(d) incubating said transformants, causing said transformants to express said deoxyribonucleic acid and produce a human physiologically active polypeptide; and (e) isolating said human physiologically active polypeptide from the incubated transformants.

According to the method of the present invention, the above-described polydeoxyribonucleic acid of the present invention is ligated to a replicable expression vehicle as a vector to obtain a replicable recombinant DNA containing the above-mentioned polydeoxyribonucleic acid. A microorganism or cell culture is transformed with the thus obtained replicable recombinant DNA to obtain a transformed microorganism or cell culture containing the recombinant DNA. The thus obtained transformant is isolated from the parent microorganism or cell culture by means of a phenotypical trait imparted with the DNA. The thus obtained transformed microorganism or cell culture is grown to effect expression of the genetic information that is encoded on the above-mentioned deoxyribonucleic acid, thereby producing a physiologically active polypeptide according to the present invention.

Furthermore, the present invention is directed to a human TNF, in mature form, secreted from host cells as a direct expression product. As a process for obtaining such a mature human TNF, there may be mentioned, for example, a process comprising constructing a DNA sequence so as to bond an amino acid sequence, known as a signal peptide, composed of from 15 to 40 amino acids that is derived from a microorganism or higher animal to the terminus of the amino acid sequence of the mature TNF.

The human TNF may be obtained as follows:

1. A bacteriophage λ/rabbit genomic library and a bacteriophage λ/human genomic library prepared by Prof. T. Maniatis, Department of Biochemistry and Molecular Biology, Harvard University, 7 Divinity Avenue, Cambridge, Mass. 02138, U.S.A. are used. These materials may be prepared according to the following procedures [see Cell, 15, p. 687 (1978)]:

(1) rabbit or human tissues, for example rabbit or human pancreas tissue, are reduced to frozen powder and treated to digest RNA and protein materials and provide, on precipitation, high molecular weight rabbit or human DNA;

(2) the high molecular weight DNA is partially digested for random cutting with respect to gene locus;

(3) the resultant DNA fragments are size-fractionated giving from 15 to 20 kilo base pair (kb) fragments;

(4) the resultant fragments of Step 3 are cloned using a λ Charon 4A phage vector; and (5) the resultant vectors are packaged in vitro to infectious phage particles containing rDNA to obtain the above-mentioned rabbit or human genomic library.

2. The rabbit TNF cDNA obtained in Reference Example 3 is $^{32}$p-labelled by P. W. J. Rigby et al's nick translation method [see J. Mol. Biol. 113, p. 237 (1977)].

3. Each of the bacteriophage λ/rabbit genomic library and bacteriophage λ/human genomic library is plated to virtual confluence on a lawn of bacteria and screened for hybridization with the $^{32}$p-labelled rabbit TNF cDNA.

4. From the appropriate clones, the corresponding DNA is isolated, restriction mapped and analyzed by Southern hybridization [see E. M. Southern, J. Mol. Biol., 98, p. 503 (1975)].

Restriction fragments containing rabbit or human TNF genes are subcloned into plasmid vectors and then sequenced.

5. The base sequence of the rabbit TNF cDNA is compared with that of the rabbit TNF gene to determine the exons (certain sequences of bases which code for the amino acid sequence of rabbit TNF) and introns (certain sequences of bases which do not code for the amino acid sequence of rabbit TNF) of the rabbit TNF gene.

6. Thereafter, the base sequence of the human TNF gene is compared with that of the rabbit TNF gene to determine the exons and introns of the human TNF gene.

7. The amino acid sequence of rabbit TNF that has been deduced from the base sequence obtained by deleting the introns of the rabbit TNF gene and combining the exons thereof is affirmed to be in agreement with that deduced from the base sequence of the rabbit TNF cDNA.

8. Next, the amino acid sequence of human TNF is deduced from the base sequence of the DNA coding for human TNF obtained by deleting the introns of the human TNF gene and combining the exons thereof. The amino acid sequence of the human TNF is affirmed to be partially in agreement with that of the rabbit TNF.

9. Then, the DNA coding for human TNF is tailored in vitro for insertion into an appropriate expression vehicle to form recombinant DNA containing the coding DNA. The recombinant DNA is used to transform an appropriate host cell which is, in turn, permitted to grow in a culture and to express the desired human TNF.

10. The human TNF thus produced has 155 amino acid residues in its mature form, beginning with serine. When it has a signal peptide in its presequence, the signal peptide is very hydrophobic in character.

The foregoing discloses the procedures for obtaining the human TNF gene, the base sequence of the DNA coding for human TNF and the process for producing the human TNF by the use of the DNA. However, it should be understood that the foregoing disclosure is not intended to limit the invention and that obvious changes may be made by those skilled in the art without changing the essential characteristics and the basic concept of the invention.

Due to the variable use frequency of a codon (genetic code) corresponding to each amino acid and for other reasons, a partial or entire portion of the base sequence of the DNA coding for human TNF may be substituted by an organic chemically synthesized artificial DNA without causing the amino acid sequence of the polypeptide obtained therefrom to be changed.

Presumably, the human TNF may be intracellularly produced in immature form as a prepeptide or prepropeptide, which may be processed via an intermediate form to a mature TNF in the processing stage. The immature form of human TNF may be deduced from the base sequence of the human TNF gene. The TNF DNA comprising a DNA encoding the TNF in immature or intermediate form may also be recombined with a natural or artificially synthesized DNA.

One application of this technique may be attained by inserting the methionine codon (ATG) in the 5'-end and inserting at least one stop codon selected from TAA, TAG and TGA in the 3'-end of the mature or intermediate or immature TNF DNA. Due to the presence of the methionine codon, the mature or intermediate or immature TNF may be produced on the mRNA synthesized with the aid of an appropriate promoter. However, the methionine residue attached to the N-terminus of the TNF is cleaved or not cleaved according to the kind of the host cell employed. The purpose of inserting the stop codon is to stop translation of the mRNA transcripted from the TNF DNA at an appropriate position (C-terminus of polypeptide of the formula I).

Another application of this technique may be attained by adding to the DNA a highly hydrophobic base sequence known as a "signal sequence". By this addition, it may become feasible to secrete the TNF to outside the host cell or, in the case of a gram-negative bacteria, into the space known as "periplasm".

When a vector in which a start codon is incorporated is employed, a fused peptide may be produced which consists of the human TNF and a peptide attributed to the vector. In this case, the fused peptide may be cleaved chemically or enzymatically. Alternatively, the fused peptide, if the main activity of the human TNF is not adversely affected, may be used as it is.

The human TNF DNA may be connected, at its region upstream of the 5'-end, to the gene sequence of a promoter thereby to obtain a TNF DNA-promoter sequence which does not hinder its replication and does not cause translation of the resultant RNA to be adversely affected. The thus obtained TNF DNA-promoter sequence may be combined with a vector which is replicable in a bacterium or higher organism cell to obtain a recombinant gene. The thus obtained recombinant gene may be used to transform a bacterium or higher organism cell used as a host. The thus obtained transformant may be cultured to effect expression of the TNF gene in order to produce the human TNF.

When *Escherichia coli* is used as the above-mentioned host, there may be mentioned, as the suitable host, various mutant strains of *E. coli* K-12, such as HB101(ATCC 33694), C600K(ATCC33955), D1210, RRI(ATCC31343), MC1061, LE392 (ATCC33572), JM101(ATCC33876), JM83 and χ1776(ATCC31244). When the *E. coli* is employed, there may be mentioned, as the suitable vector, plasmids such as pBR322, pBR325, pBR327, pUC8, pUC9, pMB9(ATCC37019), pJB8(ATCC37074) and pKC7(ATCC37084), λ phages such as λgt, λB and Charon 4A, and M13 phage. To have TNF produced in the *E. coli* cell, a promoter selected from the promoters of the *E. coli* and phage genes may be employed. Examples of the suitable promoter include the genes for lactose degradation enzyme (LAC), UV5 mutant thereof, penicillinase (BLA) and tryptophan synthetase (TRP), λ phage $P_L$ promoter and TAC promoter which is a fused promoter of tryptophan synthetase and lactose degradation enzyme.

When *Bacillus subtilis* is used as the host, there may be mentioned, as the suitable host, BD170 strain (ATCC33608), BR151 strain (ATCC33677) and MI112 strain (ATCC33712). When the *Bacillus subtilis* host is employed, there may be mentioned, as the suitable vector, plasmids pC194(ATCC37034), pUB110(ATCC37015), pSA2100(ATCC37014) and pE194. Further, when the *Bacillus subtilis* host is employed, there may be mentioned, as the suitable promoter, the genes for chloramphenicol acetylation enzyme (CAT), penicillinase and anti-erythromycin.

When a yeast is used as the host, there may be mentioned, as the suitable host, strains of *Saccharomyces cerevisiae* such as RH218(ATCC44076), SHY1-(ATCC44769), SHY3(ATCC44771), D131A, 483 and 830. When the yeast host is employed, there may be mentioned, as the suitable vector, plasmids such as YEp13(ATCC37115), YEp6, YRp7 and YIp5. Further, when the yeast host is employed, there may be mentioned, as the suitable promoter, the genes for acid phosphatase, alcohol dehydrogenase (ADHI), tryptophan synthetase (TRP), phosphoglycerate kinase (PGK), cytochrome B(COB) and actin.

When a higher organism cell culture is used as the host, there may be mentioned, as the suitable host, the cell cultures of monkey kidney, COS and mouse C127(ATCC 1616). When the higher organism cell culture host is employed, there may be mentioned, as the suitable vector, SV40 virus and The novel human physiologically active polypeptide of the present invention induces necrosis of tumors with no toxic effect upon the normal tissues of the living body. The active polypeptide of the present invention may be formulated according to known methods to prepare pharmaceutical compositions which are useful for the inhibition of cell proliferation, e.g. malignant tumor cells proliferation. The active polypeptide may be combined in admixture with a pharmaceutically acceptable carrier vehicle. An effective amount of the active polypeptide of the present invention may be mixed with a suitable amount of vehicle in order to prepare pharmaceutically acceptable compositions suitable for effective administration to the recipient.

The physiologically active polypeptide of the present invention may be administered, to subjects requiring antitumor or antiviral treatment, as an injection, eye drop, nasal drop, inhalant, external preparation, oral administration, rectal administration or vaginal tablet. The daily dose of the polypeptide of the present invention per adult may be generally in the range from 50 to 100,000,000 units. It may be preferably in the range of from 50 to 500,000 units in the case of local administration, from 1,000 to 1,000,000 units in the case of general injection such as intravenous injection and intramuscular injection, and from 10,000 to 100,000,000 units in the case of oral administration. The daily dose may be increased or decreased according to the direction for use and symptom of recipient.

The terminology "1 unit" used above means a quantity of the physiologically active polypeptide of the present invention by which 50% of $1 \times 10^5$ cells/ml of L-M cells (American Type Culture Collection CCL 1.2) are killed. The above-mentioned quantity is measured as follows. As culture vessels, there are employed 96-well microtiter plates produced by Flow Laboratories, Inc. (U.S.A.), and L-M cells are cultured in Eagle's minimum essential medium containing 1 v/v % of bovine fetal serum [the composition of this medium is described, for example, in Tissue Culture, edited by Junnosuke Nakai et al, Asakura Shoten, Japan (1967)]. A sample (0.1 ml) serially diluted with the medium and the L-M cell suspension (0.1 ml, $1 \times 10^5$ cells/ml) are mixed into each well of the plates and the plates are incubated at 37° C. for 48 hours in air containing 5% carbon dioxide. At the end of the culture period, 20 μl of glutaraldehyde is added to fix the cells. After fixation, the plates are washed with distilled water and allowed to dry, and 0.05% methylene blue (0.1 ml) is added to stain the viable cells. The plates are thoroughly washed with distilled water to remove excess dye and allowed to dry. 0.36 N Hydrochloric acid is added to each well to extract the dye from stained cells. Absorbance of each well at 665 nm is measured with Titertek Multiskan produced by Flow Laboratories, Inc. The absorbance is proportional to the number of viable cells. The above-mentioned quantity of the physiologically active polypeptide of the present invention by which 50% of $1\times10^5$ cell/ml of L-M are killed is obtained by plotting the dilution versus the absorbance on a graph.

The physiologically active polypeptide of the present invention may be suitably administered parenterally. In the parenteral preparation, there may be incorporated, as an additive, a stabilizer such as albumin, gelatin, globulin, protamine, salt of protamine or the like, a thickener such as sucrose, glycerine, methylcellulose, carboxymethylcellulose or the like and/or a pH adjusting agent such as various inorganic salts. The polypeptide may also be suitable administered in the form of a tablet. In the tablet, there may be incorporated, as an additive, a vehicle such as starch, lactose or the like in addition to the above-mentioned stabilizer.

As a result of animal experiment, it has been found that a mouse tumor is completely healed by one or two injections only, in most cases. In particular, an aliquot of artificial neoplastic cells (Meth-A cells) were transplanted to the skin of each mouse. When the tumor grew to have a diameter of 6 to 7 mm, as little as 0.6 μg of the polypeptide of the present invention was injected. A week later, a scab appeared. Two weeks later, hairs began to grow, which meant complete healing of the tumor. Later, pregnancy and successful birth were observed for the mice.

The present invention will be described in more detail with reference to the following Referential Examples and Working Examples, which should not be construed to be limiting the scope of the present invention.

In practicing the present invention, construction of a recombinant DNA and insertion of a recombinant DNA to a microorganism are carried out in accordance with the procedure described in the following experimental reports [Literatures (1) to (4)], unless otherwise indicated.

(1) Yasutaka Takagi, Manual For Genetic Engineering, Kodan-sha, Tokyo.
(2) Yasutaka Takagi, Experimental Method in Genetic Engineering, Kodan-sha, Tokyo.
(3) T. Maniatis, E. F. Fritsch, J. Sam Brook, Molecular Cloning, Cold Spring Harbor Laboratory, NY.
(4) Ray Wu et al., Method in Enzymology, Vol. 101, Academic Press, NY.

Abbreviations used in Referential Examples and Examples

MOPS: morpholinopropanesulfonic acid
LB medium: Luria-Bertani medium
DMSO: dimethylsulfoxide
PFU: plaque forming unit
EDTA: ethylenediaminetetraacetic acid
SDS: sodium dodecyl sulfate
BRL: Bethesda Research Laboratories Inc.
DMT: dimethoxytrityl
lac: lactose
Tris: tris(hydroxymethyl)aminomethane
XAR-5: X-ray film manufactured and sold by Eastman Kodak Company, U.S.A.
$1\times$SSC: 0.15 M NaCl+0.015 sodium citrate, pH7
$2\times$SSC: 0.30 M NaCl+0.030 M sodium citrate, pH7
$3\times$SSC: 0.45 M NaCl+0.045 M sodium citrate, pH7
$5\times$SSC: 0.75 M NaCl+0.075 M sodium citrate, pH7
$6\times$SSC: 0.9 M NaCl+0.09 M sodium citrate, pH7
FDSS:
  50% deionized formamide+$5\times$Denhardt's+$5\times$SSPE+0.1% SDS+100, μg/ml denatured calf thymus DNA
SSPE: 0.18 M NaCl+10 mM NaH$_2$PO$_4$+1 mM EDTA, pH 7.4
SM: phage storage medium which contains 5.8 g of NaCl 2 g of MgSO$_4$·7H$_2$O, 50 ml of 1 M Tris·Cl(pH 7.5) and 5 ml of 2% gelatin per liter
NZ-broth: medium which contains 10 g of NZ amine, 5 g of NaCl and 2 g of MgSO$_4$·7H$_2$O (NZ amine is a Type-A hydrolysate of casein manufactured and sold by Humko Sheffield Chemical Division of Kraft, Inc., U.S.A.)
IPTG: isopropyl thiogalactoside
x-gal: 5-bromo-4-chloro-3-indolylgalactoside
TAE; 0.04 M Tris-acetate (pH 8.0)—0.002 M EDTA
$5\times$Denhardt's solution: an aqueous solution containing Ficoll 1000 mg, polyvinylpyrrolidone 1000 mg and BSA 1000 mg per liter
bp: base pair Referential Example 1 (Evaluation of cytotoxic activity against L cells)

The evaluation of the cytotoxic activity of the physiologically active substance prepared in the following Referential Examples and Examples against L cells is effected by measuring its cytotoxic effect on the L929 cells (American Type Culture Collection CCL1), in accordance with the method of Ruff et al [see Lymphokines, Vol. 2, edited by E. Pick, Academic Press, N.Y., P 235 (1981)] or the method described in J. Immunol, 126, p. 1279 (1981). The method of evaluation of the cytotoxic activity of the physiologically active substance prepared in the following Referential Examples and Examples is explained below.

As culture vessels, there are employed 96-well microtiter plates produced by Flow Laboratories, Inc. (U.S.A.), and L929 cells are cultured in Eagle's minimum essential medium containing 1 v/v % of fetal calf serum and 5 μg/ml (final concentration) of actinomycin D [the composition of this medium is described, for example, in Tissue Culture, edited by Junnosuke Nakai et al, Asakura Shoten, Japan (1967)]. A sample (0.1 ml) serially diluted with the medium and the L929 cell suspension (0.1 ml, $1\times10^5$ cells) are mixed in each well of the plates and the plates are incubated at 37° C. for 21 hours in air containing 5% carbon dioxide. At the end of the culture period, 20 μl of a 20% aqueous solution of glutaraldehyde is added to fix the cells. After fixation, the plates are washed with distilled water and allowed to dry, and 0.05% methylene blue (0.1 ml) is added to obtain the viable cells. The plates are thoroughly washed with distilled water to remove excess dye and allowed to dry. 0.36 N Hydrochloric acid is added to each well to extract the dye from stained cells. Absorbance of each well at 665 nm is measured with Titertek Multiskan (produced by Flow Laboratories, Inc., U.S.A.). The absorbance is proportional to the number of viable cells. The cytotoxic activity of the physiologically active substance, unit/ml, is defined as the reciprocal dilution of the physiologically active substance that causes 50% cytotoxicity, and can be obtained by plotting the dilution versus the absorbance on a graph. The "1 unit" used in Referential Examples means a quantity of the rabbit TNF by which 50% of $10^5$ cells/ml of L929 cells are killed.

On the other hand, the amount of protein is determined by a method in which Coomassie Brilliant Blue G250 is bonded to protein, according to the teaching of Brandford et al [see Anal. Biochem. Vol. 72, pp 248–254 (1976)].

Referential Example 2

Step 1

(Preparation of TNF from rabbit serum)

Female rabbits, weighing 2.5 to 3 kg, are injected with 50 mg of formalin-killed *Propionibacterium acnes* (*Coryne-bacterium parvum*; Wellcome Research Laboratories, England) through the ear vein. Eight days later, 100 μg of endotoxin (lipopolysaccharide from *Escherichia coli* 026:B6, produced by Difco Laboratories, U.S.A.) is injected again through the ear vein and 2 hours later whole blood is collected from the heart. To the collected blood, heparin sodium is added in an amount of 100 units per 100 ml. The blood is then centrifuged while cooling at 5,000 rpm for 30 minutes to remove blood cells and insoluble solids. As a result, a plasma (2.4 liters) having a serum TNF cytotoxic activity of $3 \times 10^4$ units/ml is obtained from 40 rabbits.

Step 2

(Partial purification of TNF from rabbit serum)

To the plasma (2.4 liters) obtained in Step 1, is added 24 g of cellite. The resultant is stirred for one hour, and then subjected to filtration. The filtrate is mixed with 1.2 liters of 0.04M Tris-HCl buffer (pH 7.8), and then applied to a column of DEAE-Sepharose CL-6B (manufactured and sold by Pharmacia Fine Chemicals, Inc. Sweden) sufficiently equilibrated with 0.04M Tris-HCl buffer (pH 7.8) containing 0.1M NaCl. The column is washed with 0.04M Tris-HCl buffer, and the adsorbed TNF is eluted with 0.04M Tris-HCl buffer (pH 7.2) containing 0.18M NaCl. Fractions exhibiting cytotoxic activities against L cells are concentrated by ultrafiltration. The so obtained concentrate is applied to a column of Sephacryl S-200 (manufactured and sold by Pharmacia Fine Chemicals, Inc. Sweden) sufficiently equilibrated with 5 mM phosphate buffer, and gel-filtered using the same buffer. The active fractions are concentrated by ultrafiltration, whereby a purified TNF having an activity of $3.5 \times 10^6$ units and a specific activity of $18 \times 10^6$ units/mg is obtained. 048792261

Step 3

(Anti-TNF antibody)

The rabbit serum TNF partially purified in Step 2 is mixed with complete Freund's adjuvant (1:1), and then injected subcutaneously at the back of a 12 week age BALB/C male mouse. The above operation is repeated 2 and 4 weeks after the initial injection. One week after the last injection, whole blood is collected. From the collected blood, a serum is obtained.

The so-obtained serum is added to the culture medium for evaluation of the cytotoxic activity of TNF against L cells in such an amount that it is diluted 500-fold in final concentration. The cytotoxic activity of the rabbit serum TNF against L cells is evaluated in the same manner as described in Referential Example 1. It is found that the rabbit serum TNF exhibits no cytotoxicity against L cells. From the above result, it can be concluded that the mouse serum obtained in this contains an antibody to the rabbit serum TNF (hereinafter referred to as "anti-TNF antibody").

Referential Example 3

Step 1

(Preparation of TNF-producing cells)

A female rabbit is injected intravenously with formalin-killed cells of *Propionibacterium acnes* (*Coryne bacterium parvum*; Wellcome Research Laboratories, England). Seven days later, the rabbit is subjected to tracheotomy, and the lung is washed with a physiological saline solution, whereby floating cells are obtained. The so obtained cells are washed with a physiological saline solution. Using as a culture medium RPMI 1640 (Flow laboratories Inc., U.S.A.) containing 10 v/v % fetal calf serum, the cells are incubated at 37° C. in air containing 5% carbon dioxide. The cell culture is divided into two groups, and to one of them endotoxin derived from *Escherichia coli* (lipopolysaccharide from Escherchia coli 026:B6, produced by Difco Laboratories, U.S.A.) is added at a concentration of 10 μg/ml. the same amount of sterile water is added to the other. The supernatant of the cell culture to which endotoxin is added exhibits cytotoxic activity against L cells, and the activity reaches the maximum value within seven hours. Such activity is dissipated by the anti-TNF antibody, but is not dissipated by the normal mouse serum.

On the other hand, the supernatent of the cell culture to which no endotoxin is added exhibits no cytotoxicity against L cells.

Step 2

(Molecular weight of TNF)

To the cell culture prepared in Step 1 to which endotoxin is added, radioactive L-[$^{35}$S] methionine (1300 Ci/mmol, produced by Amersham Industries plc, England) is further added (1 mCi/ml). In accordance with the method of Laemmli [see Laemmli, U.K. (1970), Nature (London), Vol. 227, pp 680–685], the supernatant is analyzed by the SDS-polyacrylamide gel electrophoresis. The gel concentration is adjusted to 12.5 wt %. After the electrophoresis, the gel is treated with ENHANCE ® (trademark of a product of New England Nuclear Inc., U.S.A.), and after drying, is exposed to X-ray film (Fuji RX, manufactured and sold by Fuji Photo Film Co., Ltd., Japan). In the supernatant of the cell culture in the presence of endotoxin, it is observed that a substance having a molecular weight of about 17500 is formed.

Further, the supernatant of each cell culture prepared in Step 1 is subjected to SD-polyacrylamide gel electrophoresis in the same manner as described above. Thereafter, the gel is shaken in 2.5% NP 40 ® (a surface active agent sold by Calbiochem, U.S.A.) for one hour, and then in water for two hours. After shaking, each migration lane is separated by cutting, and cut into strips of 2 mm-width in a direction perpendicular to the direction of migration. Each strip is cultured with L cells, and evaluated for cytotoxic activity against L cells. In the lane on which the supernatant of the cell culture containing endotoxin is developed, cytotoxicity against L cells is observed at a position corresponding to the molecular weight of 17500. No cytotoxicity is observed at other positions.

Step 3

(Extraction of mRNA)

The cell culture as prepared in Step 1 is incubated for 2 hours after addition of endotoxin, followed by centrifugation to collect cells. Extraction of cytoplasmic RNA from the collected cells and extraction of mRNA from the cytoplasmic RNA are effected in accordance with the method of Chirgwin et al [see Chirgwin, J. M. et al, Biochemistry, Vol. 18, p. 5294 (1979)]. 4 ml of a 4M guanidine thiocyanate solution is added to $3 \times 10^8$ cells, and the mixture is pulverized by means of a homogenizer (Model: AM-7, manufactured and sold by Nihon Seiki Seisakusho, Japan). The residues are removed by centrifugation, and 2.4 g of cesium chloride is dissolved therein. The mixture is carefully poured into a polyallomer tube in which 2.5 ml of 5.7M cesium chloride and 0.1M EDTA solution (pH 7.5) has been loaded in advance, and then subjected to ultracentrifugation at 30,000 rpm for 12 hours at 20° C. using Beckman SW41 rotor (manufactured and sold by Beckman Instrument, U.S.A.). After removal of the supernatant, the pellet is dissolved in 1 ml of 10 mM Tri-HCl buffer (containing 5 mM EDTA and 1 w/v % SDS). The resulting solution is extracted with a 4:1 by volume mixture of chloroform and 1-butanol. to the aqueous phase, 0.05 volume of 2M sodium acetate and 2.5 volumes of ethanol are added, and allowed to stand at $-20°$ C. for 2 hours or more, thereby to precipitate RNA. The precipitate is collected by centrifugation, dried, and then dissolved in 500 µl of sterile water. As a result, a cytoplasmic RNA solution is obtained.

The above-obtained RNA solution is heated at 68° C. for 2 minutes, and thereafter, chilled quickly. 500 µl of 2-fold concentration 10 mM Tris-EDTA buffer (pH 7.4) (containing 1 mM EDTA, 0.1 w/v % SDS and 0.5M lithium chloride) is added to the solution, and the mixture is applied to a 200 mg oligo dT-cellulose (manufactured and sold by Bethesda Research Laboratories, Inc., U.S.A.) column, and washed with 10 ml of the same buffer (one-fold concentration) as described above. The material retained by the column is eluted with 2 ml of an elution buffer containing 10 mM Tris-HCl buffer pH 7.4, 1 mM EDTA and 0.1 w/v % SDS. To the eluate, is added 0.05 volume of sodium acetate solution and 2.5 volumes of ethanol, and the mixture is cooled at $-20°$ C. to precipitate. The precipitate is collected by centrifugation, and applied to the oligo dT-cellulose column, and the fractions adsorbed onto the oligo dT-cellulose are collected. 85 µg of mRNA is recovered as determined by the ultraviolet spectrum analysis.

Step 4

(Size fractionation of mRNA)

880 µg of mRNA prepared by the same method as described in Step 3 is dissolved in 250 µl of water, and the resulting solution is layered onto a 10 ml 5-25% linear sucrose density gradient. The sucrose density gradient is prepared by means of ISCO 570 gradienter (manufactured and sold by ISCO Inc., U.S.A.), using Tris buffer solutions [containing 25 mM Tris-HCl (pH 7.2), 2 mM EDTA and 1 w/v % SDS] respectively containing 5% sucrose and 25% sucrose.

Using Beckman SW41 rotor, ultracentrifugation is effected at 40000 rpm for 12 hours at 4° C., and fractions each of 400 µl are recovered by means of a fraction recovering apparatus (manufactured and sold by Beckman Instrument, U.S.A.), and then ethanol precipitated. The precipitated fractions are centrifuged, and dissolved in sterile water.

Step 5

(Experiment on translation of mRNA)

Translation of mRNA using oocytes of xenopus laevis (Hamamatsu biological teaching materials) is conducted according to the procedure described in the experimental reports (for example, Hiroshi Teraoka, Mikio Itsuki and Kentaro Tanaka, "Protein, Nucleic acid, Enzyme", Generetic Engineering, extra edition., 1981, p 602). Xenopus laevis is procured from Hamamatsu biological teaching materials. Fractionated mRNA obtained in Step 4 is dissolved in sterile water to have a concentration of 1 µg/µl, and the solution is injected into oocytes in such a small amount as 50 nl per cell. Cells are then cultered for 24 hours in a Barth's solution [containing 7.5 mM Tris-HCl (pH 7.6), 88 mM NaCl, 1 mM potassium chloride, 0.33 mM calcium nitrate, 0.41 mM calcium chloride, 0.82 mM magnesium sulfate, 2.4 mM sodium bicarbonate, 18 U/ml penicillin G and 18 µg/ml streptomycin] which contains 1 mg/ml bovine serum albumin. Oocytes are crushed, in the culture liquid, by means of a glass bar. The culture liquid is then centrifuged, and the supernatant is evaluated for the cytotoxic activity against L cells. mRNA which will be translated to give a polypeptide having maximum activity sediments as 16 S in size. This activity is eliminated by the anti-TNF antibody obtained in Step 3 of Referential Example 2, but is not eliminated by the normal mouse serum.

Step 6

(Preparation of transormants)

Using 5 µg of the fractionated mRNA obtained in Step 4, a double stranded DNA is prepared in accordance with procedure described in Literature (1), from page 96. As the reverse transcriptase, use is made of a product of Life Science, Inc., U.S.A. The double stranded DNA is size-fractionated on a 3.5% polyacrylamide gel, and 330 ng fraction of about 1000 to 2000 bp is obtained. In accordance with the procedure described in Literature (1), 7 ng of this fraction is extended with deoxyC residues using terminal deoxynucleotidyl transferase (manufactured and sold by Bethesda Research Laboratories, Inc., U.S.A.) and annealed with 56 ng of plasmid pBR322 which has been digested with *PstI* and extended with deoxyG residues. The so-annealed mixture is inserted into *E. coli* K-12 strain (HB101, ATCC 33694) to transform the strain. As a result, 12000 transformants are obtained.

Step 7

(Partial amino acid sequence of rabbit TNF)

Rabbit TNF partially purified in Referential Example 2 (activity: $5 \times 10^7$ units) is subjected to SDS-polyacrylamide gel electrophoresis for purification as in Step 2. Part of the gel is dyed with Coomassie Brilliant Blue. A band at the position corresponding to the molecular weight of 17000 is cut out from the gel, and extracted with 1% ammonium bicarbonate. About 180µg of TNF is recovered as protein.

150 µg of the recovered TNF is dissolved in 75 µl of 1% ammonium bicarbonate, followed by addition of 3 µg of TPCK trypsin (manufactured and sold by Worthington Biochemical, U.S.A.). The mixture is incubated at 37° C. for 4 hours. The mixture is then fractionated by means a high performance liquid chromatography column comprising Cosmosil 5C8 (manufactured and sold by Nakariai Chemical, Ltd., Japan) as the packing material, thereby to obtain fragments digested with trypsin.

The highly purified TNF and the trypsin-digested fragments thereof are then subjected to desalting by means of Sephadex G-25 column, and then freeze-dried. According to the method of R. M. Hewick et al (see J. Biol. Chem., Vol. 256, pp 7990-7997, 1981), the purified TNF and the trypsin-digested fragments are each subjected to Edman Degradation from the N-terminal. PTH-amino acid liberated in each step is analyzed by the customary method by means of a high performance chromatography model SP8100 (manufactured and sold by Spectra physics, U.S.A.) using Zorbax ODS (manufactured and sold by E.I. Du pont, U.S.A.) as the column. As a result, it is found that the TNF has the following N-terminal amino acid sequence: Ser-Ala-Ser-Arg-Ala-Leu-Ser-Asp-Lys-Pro-Leu-Ala-His-Val-Val-Ala-Asn-Pro-Gln-Val-Glu-Gly-Gln-Leu-Gln-.

One of the trypsin-digested fragments has the following N-terminal amino acid sequence. Glu Thr Pro Glu Glu Ala Glu Pro Met Ala

Step 8
(Synthesis of Oligodeoxynulcleotide probe)

Oligodeoxynucleotides complementary to the base sequence of the mRNA which is deduced from the amino acid sequence of rabbit TNF obtained in Step 7 of Referential Example 3 is synthesized according to the improved phosphotriester method which has already been reported by the present inventor in H. Ito et al, "Nucleic Acid Res." 10, 1755-1769 (1982). In preparing oligodeoxynucleotides, 128 oligodeoxynucleotides estimated from the amino acid sequence of rabbit TNF are classified into five groups, namely groups of 16, 16, 32, 32 and 32 and are synthesized as mixtures of oligodeoxynucleotides of the respective groups. The obtained oligodeoxynucleotides of the respective groups are deprotected according to the customary method and purified by column chromatography using Sephadex G-50 (manufactured and sold by Pharmacia Fine Chemicals, Inc., Sweden), electrophoresis on a 20% by weight polyacrylamide gel containing 7M of urea and column chromatography using DE52 (manufactured and sold by Whatman Ltd., U.S.A.). The thus obtained oligodeoxynucleotides of the respective groups are dialyzed against 0.1 mM Tris-EDTA buffer solution.

Each of the purified oligodeoxynucleotides of the respective groups is labelled using $T_4$ polynucleotide kinase (manufactured and sold by Bethesda Research Laboratories, Inc., U.S.A.) and $\alpha$-$^{32}$P-adenosine triphosphate according to the customary method and then purified by column chromatography using DE52 (manufactured and sold by Whatman Ltd., U.S.A.). The radioactive material is incorporated into each of oligodeoxynucleotides of the respective groups in an amount of about $3 \times 10^8$ cpm/$\mu$g. The oligodeoxynucleotide probes each obtained in the form of a mixture of the respective group are designated as shown in Table 1.

Part of the amino acid sequence of the rabbit TNF, the base sequence of the mRNA estimated from the amino acid sequence of the rabbit TNF and the base sequences of synthetic oligodeoxynucleotide probes of the respective groups are shown in Table 1.

TABLE 1

| Amino acid sequence | Carboxyl terminal ... | | | | | | | | Amino terminal |
|---|---|---|---|---|---|---|---|---|---|
| | | Ala | Met | Pro | Glu | Ala | Glu | Glu ... | |
| m RNA | 3'... | XCG | GTA | XCC | YAG | XCG | YAG | YAG ... | 5' |
| Probe MH | 5' | GC | CAT | MGG | MTC | GGC | MTC | MTC | 3' |
| Probe MI | 5' | GC | CAT | NGG | MTC | GGC | MTC | MTC | 3' |
| Probe MJ | 5' | GC | CAT | ZGG | MTC | AGC | MTC | MTC | 3' |
| Probe MK | 5' | GC | CAT | ZGG | MTC | CGC | MTC | MTC | 3' |
| Probe ML | 5' | GC | CAT | ZGG | MTC | TGC | MTC | MTC | 3' |

Note:
X represents a ribonucleic acid residue of A,C,G or U.
Y represents a ribonucleic acid residue of A or G.
M represents a deoxyribonucleic acid residue of T or C.
N represents a deoxyribonucleic acid residue of A or G.
Z represents a deoxyribonucleic acid residue of A, C, G or T.

mRNA of the cells producing TNF which is obtained according to Step 3 of Referential Example 3 is treated with a solution containing 1M of glyoxal, 10 mM of NaH$_2$PO$_4$ and 50% by volume dimethyl sulfoxide at 50° C. for 60 minutes and then subjected to fractionation using electrophoresis on a 1.1% by weight agarose gel. The fractionated mRNA is transferred on a filter of an electrophoresis type transfer blotting apparatus (manufactured and sold by Bio Rad, U.S.A.) according to the manual of the maker. Then the mRNA on the filter of the apparatus is treated with a 5×Denhardt's solution containing a 5×SSC solution and 150 $\mu$g/ml of denatured salmon spermatozoa DNA at 65° C. for two hours and, then treated with a 5×Denhardt's solution containing $1 \times 10^7$ cpm/ml of the labelled oligodeozxynucleotides and a 5 x SSC solution at 50° C. for two hours. The above-obtained filter is washed with a 6 x SSC solution successively four times at room temperature, 40° C., 50° C. and 60° C. An XAR-5 X-ray film (manufactured and sold by Eastman Kodak Company, U.S.A.) is exposed to the radiation from the filter. As a result, it is found that the oligodeoxynucleotides designated by Probe MJ are most strongly hybridized with the mRNA, showing that the oligodeoxynucleotide having a base sequence which is completely complimentary to the mRNA is contained in the oligodeoxynucleotides designated by Probe MJ.

Step 9
(Cloning of TNF gene of rabbit)

In accordance with the procedure described in Literature (2), page 162, the transformants obtained in Step 6 of Referential Example 3 are transferred onto a cellulose filter and the DNA of the transformants is hybridized with the labelled oligodeoxynucleotide (Probe MJ) selected in Step 8 of Referential Example 3 under the same conditions as in Step 8 of Referential Example 3 (colony hybridization). In the just above procedure, 49 colonies which are strongly hybridized with the labelled oligodeoxynucleotides (Probe MJ) are selected and further fixed onto another nitrocellulose filter. Then, using 49 colonies, further hybridization is carried out to select nine colonies which are more strongly hybridized with the labelled oligodeoxynucleotides (Probe MJ).

In accordance with the rapid plasmid separating procedure described in Literature (1), page 6, about 5 µg plasmid is obtained from each of the nine colonies. Each of the obtained plasmids is cleaved using restriction enzymes, PstI, TaqI, RsaI and PvuII (each manufactured and sold by Bethesda Research Laboratories, Inc., U.S.A.) according to the procedure described in the manual of the maker, followed by electrophoresis effected on a 1% by weight agarose gel. Then, fragments obtained by cleavage by the respective restriction enzymes are compared with respect to length thereof.

The results suggest that all the nine strains corresponding to the nine colonies have the base sequence of the fragment obtained by cleavage by PvuII and RsaI and consisting of about 50 bp and that most of the nine strains have the base sequence of the fragment obtained by cleavage by RsaI and consisting of about 200 bp. In other words, the results suggest that the nine strains have partially common base sequences. The results of analysis by the restriction enzymes are shown in FIG. 1.

Seven strains containing plasmids designated in Table 2 below are separately cultivated in 2 ml of LB medium containing 10 µg/ml of tetracycline until the optical density of the solutions shows the values shown in Table 2 below, followed by centrifugation to obtain respective strains. Each of the obtained strains is added into 2 ml of physiological saline and disrupted by sonication. The obtained solutions are subjected to centrifugation and the cytotoxic activity against L cells of the obtained supernatants is determined. The results are shown in Table 2 below. As a blank test, the same procedures as mentioned above are repeated using a strain containing plasmid pBR322. The results are also shown in Table 2 below.

TABLE 2

| Plasmid | Number of annealed base pairs | $OD_{600}$ | Cytotoxic activity against L cells (unit/ml) |
|---|---|---|---|
| pB 2-2 | 1400 | 1.369 | 35 |
| pB 2-3 | 800 | 1.605 | <10 |
| pB 2-7 | 1060 | 1.364 | <10 |
| pR 9 | 1550 | 1.618 | <10 |
| pR 12 | 1400 | 1.458 | 15 |
| pR 18 | 1850 | 1.438 | <10 |
| pR 25 | 1350 | 1.514 | <10 |
| pBR 322 | 0 | 1.677 | <10 |

The cytotoxic activity against L cells is eliminated by anti-TNF antibody but is not eliminated by normal mouse serum. This shows that all of the above-mentioned nine colonies have plasmids which contain oligodeoxynucleotides coding for TNF.

Step 10

(Determination of base sequence of DNA coding for rabbit TNF)

E. coli strains containing plasmids pB2-7 and pR 18 are cultivated in one liter of M9 medium described in Literature (3), page 440 and containing 10 µg/ml of tetracycline. then, in accordance with procedure described in Literature (3), page 90, each of the plasmids is isolated in an amount of about 150 µg.

The base sequence of the insert of each plasmid is determined according to the Maxam-Gilbert chemical procedure described in Maxam et al "Method in Enzymology", 65, P 499 (1980), Academic Press. The thus determined base sequence is found to be in agreement with the partial amino acid sequences determined in Step 7 of Referential Example 3. Thus, the whole sequence of TNF of rabbit is considered to be elucidated.

Step 11

Figure 2:
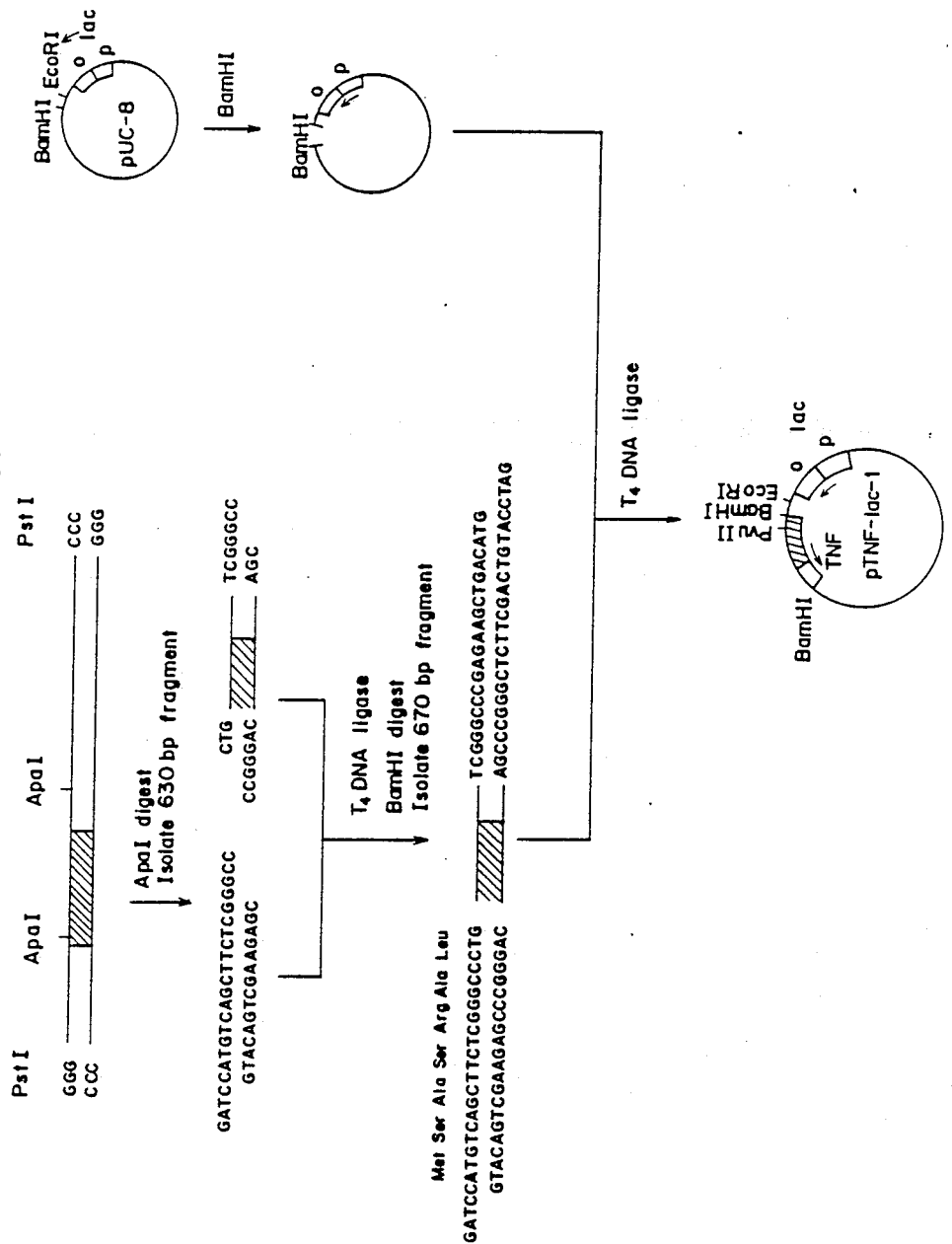
FIG. 2 illustrates the flow-sheet of the method for the preparation of a recombinant DNA (pTNF-lac-1) coding for the conventional rabbit physiologically active polypeptide.

In this step, construction of a plasmid is carried out using the recombinant plasmid pR12 to obtain direct expression of TNF in E. coli using lac as a promote. The procedures are illustratively shown in FIG. 2. First 10 µg of plasmid pR12 is digested with 10 units of ApaI (manufactured and sold by Bethesda Research Laboratories, Inc., U.S.A.) at 37° C. for two hours and electrophoresed on a 4% by weight polyacrylamide gel to isolate 630 bp fragments. About 1 µg of the fragment is isolated from the gel by electroelution. In the same manner as in Step 8 of Referential Example 3, two oligodeoxynucleotides shown in FIG. 2, namely 5'-GATCCATGTCAGCTTCTCGGGCC-3'- and 5'-CGAGAAGCTGACATG-3' are synthesized. Then, each 5' end of the oligodeoxynucleotides (about 100 pmole) is phosphorylated using $T_4$ polynucleotide kinase in accordance with the method described in Literature (3), page 122. After completion of the reaction, the reaction mixture is extracted with phenol and then with chloroform. Then the obtained synthetic oligomers are mixed with 0.5 µg of the ApaI 630 bp fragment and ethanol precipitated. The fragment is ligated with the synthetic oligomers at 4° C. overnight using 10 units of $T_4$ DNA ligase in accordance with the procedure described in Literature (1), page 37. After completion of the reaction, the reaction mixture is ethanol precipitated and digested with 20 units of BamHI at 37° C. for three hours, followed by electrophoresis effected on a 4% by weight polycrylamide gel to recover 670 bp fragment by electroelution. One µg of commercially available plasmid pUC-8 (catalog No. 4916, manufactured and sold by P-L Biochemicals, Inc., U.S.A.) is digested with BamHI and extracted with phenol and then with chloroform, followed by ethanol precipitation to obtain a vector. 0.5 µg of the obtained vector is ligated with the above-obtained fragment having BamHI sites on its both ends and containing about 670 bp coding for TNF using $T_4$ DNA ligase. In accordance with the procedure described in literature (4), page 20, E. coli is transformed using the above-obtained vector and cultivated on an agar medium containing 1 mM of IPTG and 0.004% (w/v) of X-gal to obtain about 200 white colonies. Plasmid DNA is prepared from 100 of these transformants and digested with BamHI. As a result, it is found that 15 plasmids contain the intended BamHI fragment (about 670 bp). In order to examine the direction of insertion, the above 15 plasmids are digested with EcoRI having only one recognition site on its pUC-8 and PvuII having only one recognition site on its about 670 base pair fragment part and electrophoresed on a 6% by weight polyacrylamide gel. As a result, it is determined that 7 plasmids have the intended fragment consisting of about 140 bp and that the direction of transcription of the lac promotor on pUC-8 is in agreement with that of the oligodeoxynucleotides coding for TNF.

DNA sequence analysis shows that these seven plasmids have the same sequence and have the desired nucleotide sequence at the junctions between the *lac* promoter, synthetic DNA and cDNA.

Figure 3:
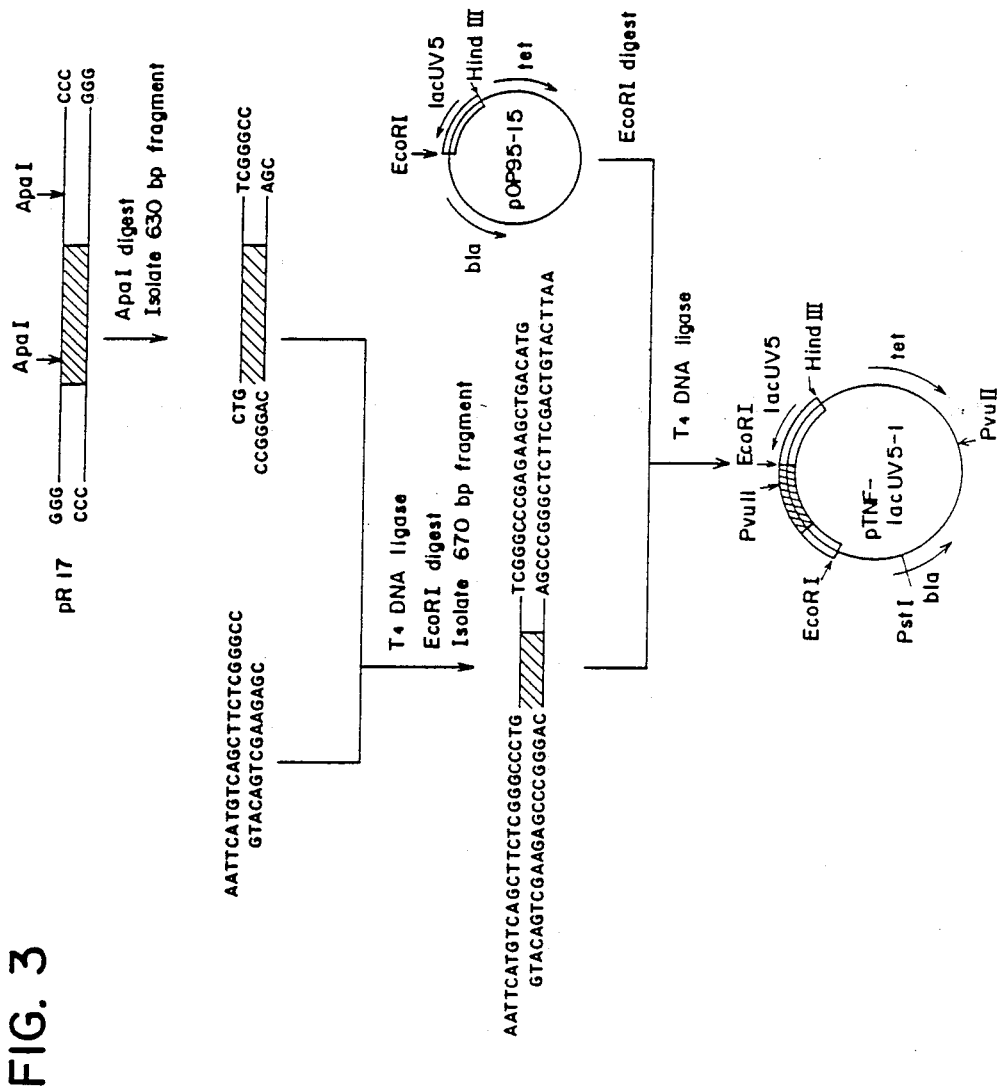
FIG. 3 illustrates the flow-sheet of the method for the preparation of another recombinant DNA (pTNF-lacUV5-1) coding for the conventional rabbit physiologically active polypeptide.

Construction of further plasmids is carried out using the recombinant plasmid pR17 in order to obtain direct expression of TNF in *E. coli* using *lac* UV5 as a promoter. The procedures are illustratively shown in FIG. 3. First, 10 μg of the plasmid pR17 is digested with 10 units of *Apa*I (manufactured and sold by Bethesda Research Laboratories, Inc. U.S.A.) at 37° C. for two hours and electrophoresed on a 4% by weight polyacrylamide gel to isolate a fragment consisting of about 630 bp. About 1 μg of the fragment is isolated from the gel by electroelution. In the same manner as in Step 8, two oligodeoxynucleotides shown in FIG. 3, namely 5'-AATTCATGTCAGCTTCTCGGGCC-3' and 5'-CGAGAAGCTGACATG-3' are synthesized. Then, each 5' end of the two oligodeoxynucleotides (about 100 pmole) is phosphorylated using T$_4$ polynucleotide kinase in accordance with the method described in Literature (3), page 122. After completion of the reaction, the reaction mixture is extracted with phenol and then with chloroform. Then the synthetic oligomers are mixed with 0.5 μg of the previously obtained *Apa*I fragment (about 630 bp) prepared from the plasmid pR17 and ethanol precipitated. The fragment is ligated with the synthetic oligomers at 4° C. overnight using 10units of T$_4$ ligase in accordance with procedure described in Literature (1), page 37. After completion of the reaction, the reaction mixture is ethanol precipitated and digested with 20 units of *Eco*RI at 37° C. for three hours, followed by electrophoresis effected on a 4% by weight polyacrylamide gel to recover a fragment (about 670 bp) by electroelution.

In accordance with the procedure described in F. Fuller, "Gene", 19, pp 42–54 (1982), plasmid pOP95-15 is prepared.

One μg of pOP95-15 is digested with *Eco*RI and extracted with phenol and then with chloroform, followed by ethanol precipitation to obtain a vector. Using T$_4$ DNA ligase, 0.5 μg of the obtained vector is ligated with the fragment (about 670 bp) obtained by ligating the synthetic oligonucleotide with the oligonucleotide coding for TNF. In accordance with the procedure described in Literature (4), page 20, *E. coli* JM101 (ATCC 33876) is transformed using the above-obtained vector and cultivated on a medium containing 1 mM of IPTG and 0.004% (w/v) of X-gal to obtain about 150 white colonies. Plasmid DNA is prepared from 100 of these colonies and digested with *Eco*RI. As a result, it is found that 12 plasmids contain the intended *Eco*RI fragment (about 670 bp). In order to examine the direction of insertion, the above 12 plasmids are digested with *Pvu*II and *Pst*I and electrophoresed on a 1.5% by weight agarose gel. As a result, it is determined that four plasmids have the desired fragments (about 1280 bp and about 2600 bp) and that the direction of transcription of the *lac* UV5 promoter is in agreement with that of the oligodeoxynucleotides coding for TNF.

Base sequence analysis shows that these four plasmids have the same sequence and that the *lac* UV5 promoter, the synthetic oligodeoxynucleotide and cDNA are properly combined with each other. The obtained plasmids are designated pTNF-lacUV5-1.

Step 12

(Purification of TNF produced by *E. coli*)

*E. coli* strains containing plasmids obtained in Step 11 are cultivated in 50 ml of LB medium containing ampicillin at 37° C. overnight. Then the strains are transferred to 5 liter of LB medium containing 100 μg/ml of ampicillin and further cultivated at 37° C. for three hours. Isopropyl-β-D-thiogalactopyranoside (manufactured and sold by Sigma Chemical Company, Inc., U.S.A.) is added to it to a final concentration of 1 mM. Further cultivation is carried out for six hours, followed by cooling. Then strains are collected by centrifugation. In the same manner as described in Step 11, the strains are added into 5 liters of 0.04M Tris-HCl buffer solution (pH 7.8) and disrupted by sonication to obtain a strain protein solution. The obtained solution has cytotoxic activity against L cells of $5 \times 10^7$ units/l.

The obtained solution is purified in the same manner as in Step 2 of Referential Example 2 to obtain $1.2 \times 10^6$ units of TNF. The specific activity of the TNF is $6.8 \times 10^7$ units/mg.

Step 13

(Evaluation using transplanted Meth A sarcoma in mouse)

$2 \times 10^5$ Meth A Sarcoma cells are transplanted intradermally in the abdominal area of a BALB/c mouse and, 7 days later, mice with tumors of 7 to 8 mm in diameter and with no spontaneous central necrosis are selected for evaluation. A sample (0.2 ml) of TNF obtained in Step 12 of Referential Example 3 and diluted with physiological saline solution is injected through the tail vein. The activity of the sample is evaluated after 24 hours according to the following criterion.

(−): no change
(+): slight hemorrhagic necrosis
(++): moderate hemorrhagic necrosis (central necrosis extending over approximately 50% of the tumor surface)
(+++): marked hemorrhagic necrosis (massive necrosis leaving a small viable rim along the tumor periphery)

20 Days after the injection of the sample, observations are made on the involution of tumors and recovery rate is determined according to the following equation.

$$\text{Recovery rate} = \frac{\text{Number of mice which had been completely recovered from tumor}}{\text{Number of mice used for test}}$$

The results are shown in Table 3.

TABLE 3

| Injected amount of rabbit TNF produced by *E. coli* units/mouse | Number of mice used for test | Evaluation for activity of samples (after 1 day) | | | | Recovery rate (after 20 days) |
|---|---|---|---|---|---|---|
| | | − | + | ++ | +++ | |
| $2 \times 10^5$ | 5 | 0 | 0 | 1 | 4 | 5/5 |
| Reference (physiological saline) | 5 | 5 | 0 | 0 | 0 | 0/5 |

Example 1

Step 1 (Transformation of E. coli K12 Strain MC1061 with pR18, pB2-7 and pB2—2 Plasmids)

Colonies of E. coli K12 strain MC1061 are transformed with each of the pR18, pB2-7 and pB2—2 plasmids, which are obtained in Reference Example 3, according to the customary procedures. Specifically, colonies of E. coli K12 strain MC1061 are cultured in LB medium until the optical density of the culture broth becomes 0.3 at 550 nm. 50 ml of the grown E. coli culture is harvested, washed with a 25 ml mixture containing 10 mM MOPS (pH7.0) and 10 mM RbCl, and resuspended in a 25 ml mixture containing 0.1M MOPS (pH6.5), 50 mM $CaCl_2$ and 10 mM RbCl. The resulting suspension is cooled on ice for 30 min, centrifuged and suspended in a mixture of 2 ml of the above-mentioned mixture containing 0.1M MOPS (pH6.5), 50 mM $CaCl_2$ and 10 mM RbCl and 30 µl of DMSO. To a 200 µl aliquot of the resulting suspension if separately added 10 µl of each of the plasmid DNA solutions. Each of the resulting mixtures is cooled on ice for 30 min, and then heat-shocked at 44° C. for 60 seconds. Immediately thereafter, 5 ml of the LB medium pre-warmed at 37° C. is added to each of the heated mixtures, followed by incubation at 37° C. for one hour. The obtained culture broths are each subjected to centrifugation to form cell pellets. The supernatant is discarded, and LB medium is added and stirred to resuspend each of the cell pellets. Each of the resulting suspensions is inoculated to an LB agar plate containing 30 µg/ml tetracycline, followed by incubation at 37° C. overnight. As a result, colonies of tetracycline-resistant transformants transformed, each, with pR18, pB2-7 and pB2—2 plasmids are obtained.

Step 2 (Preparation of pB2-7 and pB18 Plasmid DNAs)

Each of the transformants respectively transformed with pB2-7 and pR18 plasmids which are obtained in Step 1 is subjected to (1) growth of the transformant and amplification of the plasmid; (2) harvesting and lysis of the transformant, and (3) purification of the plasmid DNA, in accordance with the procedures as described at pages 88-96 of T. Maniatis, E. F. Fritsch and J. Sambrook, "Molecular Cloning", published by Cold Spring Harbor Laboratory, U.S.A. Illustratively stated, each of the transformants is inoculated into Lb medium containing 30 µg/ml tetracycline and incubated at 37° C. with vigorous shaking. This step is repeated to attain growth of the transformant and amplification of the plasmid. The transmformant culture is harvested by centrifugation at 4000 g for 10 min. at 4° C. the supernatant is discarded. The resulting pellet is washed in 100 ml of ice-cold STE [0.1M NaCl, 10 mM Tris.Cl (pH7.8) and 1 mM EDTA], and subjected to lysis by boiling in a solution of 20 mg/ml lysozyme—10 mM Tris.Cl, PH 8.0. the viscous product is transferred to an ultracentrifuge tube, and centrifuged at 25,000 rpm for 30 min at 4° C. to obtain a DNA solution. The volume of the DNA solution is measured. For every milliliter, exactly 1 g of solid cesium chloride is added and mixed gently until all of the salt is dissolved. 0.8 ml of a solution of ethidium bromide (10 mg/ml in $H_2O$) is added for every 10 ml of cesium chloride solution. The final density of the solution if 1.55 g/ml, and the concentration of ethidium bromide is approximately 600 µg/ml. The cesium chloride solution is transferred to a tube suitable for centrifugation, and the remainder of the tube is filled with light paraffin oil. Centrifugation is conducted at 45,000 rpm for 36 hours at 20° C. to obtain two bands of DNA, the upper band thereof consisting of linear bacterial DNA and nicked circular plasmid DNA and the lower band thereof consisting of closed circular plasmid DNA. The lower band of DNA is collected into a glass tube through a hypodermic needle inserted into the side of the tube. The ethidium bromide is removed, and the aqueous phase is dialyzed against TAE. The plasmid DNA solution is treated with RNase, and extracted with an equal volume of equilibrated phenol. The aqueous phase is layered on a column of Bio-Gel A-150 equilibrated in TAE (pH8.0) and 0.1% SDS. The DNA in the column is washed, and a reservoir of TE with 0.1% SDS is applied to collect fractions. The fractions are precipitated with ethanol to obtain a pure plasmid DNA.

By conducting the above procedures, 250 µg of pure pB2-7 plasmid DNA and 134 µg of pure pR18 plasmid DNA are obtained.

Step 3 (Nick Translation of Pure pB2-7 and pR18 Plasmid DNAs)

From the pure pB2-7 plasmid DNA obtained in Step 2, 40 µg is taken, digested with PstI restriction enzyme and subjected to electrophoresis through 4% acrylamide gel. After electrophoresis, the DNA is stained and the desired band is cut out to isolate a PstI insert.

Using 500 ng of the isolated PstI insert, nick translation is carried out in the manner as described in Maniatis, T. et al, proc. Natl. Acad. Sci. U.S.A., 72, 1184 (1975). For the nick translation, the Nick Translation Kit produced and sold by Bethesda Research Laboratories Inc., U.S.A. is employed, and 80 pmole of radioactive dCTP is applied in a 25-µl reaction system (at 400 Ci/mmole). To a mixture consisting of: 2.5 µl Solution A (dNTP's solution) 2.5 µl Solution B (500 ng of test DNA viz. PstI insert) 5 µl hot dCTP (3200 Ci/mmole) 1.3 µl cold dCTP (65 pmole, 50 pmole/µl dCTP) 11.2 µl Solution E ($H_2O$) 22.5 µl (total) is added 2.5 µl of Solution C (DNaseI, DNA Polymerase I), and reacted at 15° C. for 60 min. Then, Solution D (stop buffer) is added to the resulting mixture to stop the reaction. Further, carrier tRNA is added, subjected to ethanol precipitation twice and dissolved in 500 µl of water. The specific activity per µg DNA is $9.3 \times 10^7$ cpm.

With respect to the pure pR18 plasmid DNA obtained in Step 2, also, the above-described procedures are carried out to effect the nick translation. The specific activity per µg DNA is $7 \times 10^7$ cpm.

Step 4 (Preparation of RsaI Insert Fragment of pR18 Plasmid DNA)

80 µg of the pR18 plasmid DNA is digested with RsaI restriction enzyme, and subjected to electrophoresis through 4% polyacrylamide gel. The following desired bands of inserts are cut out and purified by means of the BND column:

| | |
|---|---|
| about 640 bp | 3.77 µg (recovery 52%) |
| about 175 bp | 1.77 µg (recovery 50%). |

The above about 640 bp insert is designated as 3'-fragment of pR18 (meaning 3'-untranslated region of pR18), and the above about 175 bp insert is designated as pR18-cfr (meaning coding region of pR18).

Moreover, the above procedures are repeated using PstI and MstII restriction enzymes istead of the RsaI restriction enzyme to obtain the following band:

| about 450 bp | 3.65 µg (recovery 60%) |

The above insert is designated as 5'-fragment of pR18.

Step 5

(Isolation of the Human Genomic TNF Gene)

The $^{32}$P-labelled plasmid pB2-7 insert obtained in Step 3 of Example 1 is used as a hybridization probe to screen $10^6$ plaques of bacteriophage Charon 4A/human genomic library propared by insertion into the Charon 4A EcoRI ligation site [Blattner et al, "Science" 196, 161 (1977)] of sized fragments from partially digested human DNA [Maniatis et al, "Cell" 15, 687 (1978)]. The plaque hybridization method of Benton and David [Benton and Davis, "Science", 196, 180 (1977)] is used. Since not all of the bacteriophage in the starting culture contain the necessary genetic material for preparing human TNF, a probe which has a base sequence complementary to the rabbit TNF gene is used. DNA of phage plaques having the desired genetic material incorporated the radioactive probe and ae identified by their radioactivity. Nine hybridizing plaques are isolated from the library.

The procedures and conditions used are as follows.
(1) Number of plaques: $\sim 1 \times 10^6$ plaques ($\sim 4 \times 10^4$ plaques/150 mm plate $\times$ 25)
(2) Transfer to nitrocellulose filters: [see Benton and Davis, Science, 196, 180 (1977)]
(3) Hybridization: Addition of $1.25 \times 10^5$ cpm/ml of pB2-7 insert probe prepared in Step 3 of Example 1, 42° C., 19.5 hr
(4) Washing:
   2×SSC-0.1% SDS at room temp.
   Immersion ↓ 10 min. ×4
   1×SSC-0.1% SDS at 50° C.
   Immersion 30 min. ×2
(5) Exposure:
   XAR-5 (Eastman Kodak Company, U.S.A.)
   −80° C., 2 intensifying screens, 39 hr In the above screening, 12 candidate strains are obtained. In the same manner as mentioned above, second screening is carried out to obtain nine strains containing the intended fragment. Using these strains, third screening is carried out in the same manner as mentioned above to obtain nine strains containing the intended fragment. Using the obtained strains, fourth screening is carried out to confirm that the nine strains contain the intended fragment. The obtained nine bacteriophages containing the intended fragment are designated HG-1~HG-9, respectively.

Step 6

(Isolation of Rabbit genomic TNF Gene)

Substantially the same procedure as described in Step 5 of Example 1 are repeated except that $10^6$ plaques of bacteriophage Charon 4 A/rabbit genomic library which is prepared using digested rabbit DNA [Maniatis et al, Cell, 15, 687 (1978)] instead of digested human DNA. $6.7 \times 10^5$ plaques of bacteriophage Charon 4A/rabbit genomic library are used instead of $10^6$ plaques of the bacteriophage Charon 4A/human genomic library.

Thus, there is obtained two bacteriophage strains (RG-1 and RG-2 containing the rabbit genomic TNF gene.

Step 7

(Southern blotting analysis of human clones)

Using the bacteriophages HG-3, HG6 and HG-7 obtained in Step 5 of Example 1, DNA of each bacteriophage is obtained according to the following procedures.

$6 \times 10^{10}$ cells of E. coli LE392 (host cell) are suspended in 18 ml of SM and $3 \times 10^9$ PFU of bacteriophage HG-3 is added, thus allowing the E. coli to be infected at 37° C. for 20 minutes. Then, the obtained mixture is added in 3 liters of NZ-broth and subjected to shaking culture at 37° C. for 23 hours. 60 ml of CHCl$_3$ is added to the mixture and further subjected to shaking culture for 30 minutes. NaCl is added to the mixture to a final concentratioin of 1M, the mixture is allowed to stand for 15 minutes, followed by centrifugation to obtain supernatant. The, polyethylene glycol (molecular weight: about 6000) is added to the mixture so that the concentration of polyethylene glycol becomes 10% (w/v), and allowed to stand for 22 hours at 4° C. Bacteriophages are collected by centrifugation. The obtained bacteriophages are suspended in 28 ml of SM and an equal volume of CHCl$_3$ is added. After stirring by means of Vortex for 30 seconds, the mixture is subjected to centrifiguation to obtain aqueous phase. SM is added to the aqueous phase so that the total amount becomes 30 ml. 26.4 g of CsCl is added to the obtained mixture and dissolved gently, followed by ultracentrifugation (45000 rpm, 20 hours) to obtain bacteriophages in the form of a band. The obtained mixture containing bacteriophages is dialyzed against 10 mM NaCl—50 mM Tris (pH8)—10 mM MgCl$_2$. Then, EDTA, Proteinase K and SDS are added to the mixture so that the concentrations of them are 20 mM, 50 µg/ml and 0.5% (w/v), respectively. Then the mixture is treated at 65° C. for one hour and extracted with phenol, a mixture of phenol and CHCl$_3$ (1:1 by volume) and then with CHCl$_3$. The obtained aqueous phase is dialyzed against 10 mM Tris (pH8) —1 mM EDTA. the ultraviolet absorption measurement of the obtained aqueous phase shows that pure DNA of the bacteriophage HG-3 is obtained.

Substantially the same procedures as described with respect to the preparation of DNA of the bacteriophage HG-3 are repeated to obtain DNAs of bacteriophages HG-6 and HG-7.

Thus, there are obtained 2920 µg of HG-3, 1100 µg of HG-6 and 819 µg of HG-7.

In accordance with the Southern method [E. M. Southern, J. Mol. Biol., 98, 503 (1975)], Southern blotting analysis of the obtained DNAs is performed. The procedures and conditions are as follows.

(1) DNA:

| HG-3 | 825 ng | each |
| HG-6 | 935 ng | each |
| HG-7 | 685 ng | each |

(2) Digestion with various restriction enzymes:
10 units BamHI, 10 units EcoRI,
10 units BamHI +10 units EcoRI
10 units HindIII,
10 units HindIII+10 units EcoRI
10 units PvuII 37° C., 3 hr
(3) Electrophoresis:
0.8% Agarose gel
TAE
28 V, 15.5 hr
(4) Transfer to nitrocellulose filters:
[see E. M. Southern, J. Mol. Biol., 98, 503 (1975)]
(5) Prehybridization:
30 ml FDSS
42° C., 6 hr
(6) Hybridization
5'-fragment (1×10⁵ cpm/ml) of pR18
(prepared in Step 4 of
Example 1)
42° C., 14 hr
(7) 2×SSC—0.1% SDS at room temp.
Immersion ↓ 10 min. ×4
1×SSC—0.1% SDS at 50° C.
Immersion 30 min. ×2
(8) Exposure:
XAR-5 (Eastman Kodak Company, U.S.A.)
−80° C., 2 intensifying screens, 14 hr
The results of hybridization are shown in Table 4.

TABLE 4

| Enzyme | Clone (bacterio-phage) | Hybridizing fragment size with Probe (pR18) | |
|---|---|---|---|
| | | 5' end | 3' end |
| BamHI | HG-3 | 6.7 kb | ← |
| | -6 | 11.2 kb | ← |
| | -7 | 9.2 kb | ← |
| BamHI + EcoRI | HG-3 | 2.9 kb | ← |
| | -6 | " | ← |
| | -7 | " | ← |
| EcoRI | HG-3 | " | ← |
| | -6 | " | ← |
| | -7 | " | ← |
| HindIII + EcoRI | HG-3 | " | ← |
| | -6 | " | ← |
| | -7 | " | ← |
| HindIII | HG-3 | 9.7 kb | ← |
| | -6 | 4.1 kb | ← |
| | -7 | 9.7 kb | ← |
| PvuII | HG-3 | 2.2 kb | 0.9 kb |
| | -6 | 1.9 kb | 0.9 kb |
| | -7 | 2.2 kb | 0.9 kb |

NOTE:
The symbol "←" means same fragment hybridizes.

Step 8

(Southern blotting analysis of rabbit clones)

Substantially the same procedures as in Step 7 of Example 1 are repeated except that each of the bacteriophages RG-1 and RG-2 is used instead of each of the bacteriophages HG-3, HG-6 and HG-7. Thus, there is performed Southern blotting analysis. As a result, it is found that pR18 5'-fragment is hybridized with a single band fragment of fragments which are obtained by cleavage of RG-1 and RG-2 with each of BamHI, EcoRI, BglII, HINdIII and BamHI+EcoRI.

Step 9

(Construction of bacterial clones containing human genomic TNF gene)

The method of Landy et al [Biochemistry, Vol. 13, 2134 (1974)] is used to obtain DNA of HG-3 as obtained in the above Step 5. 33 μg of the resulting HG-3 DNA is digested with 80 units of EcoRI at 37° C. for 3 hours. The digest is electrophoresed on 1% low melting agarose gel (conditions: 1×TAE, 20 V, 14.5 hr). The 2.9 kb band is isolated from the agarose gel as described by T. Maniatis [Molecular Cloning, Cold Spring Harbor Laboratory, p 377 (1982)]. Specifically, the cut-out gel of the 2.9 kb band portion is heated at 65° C. for 15 min. The EcoRI-cleaved HG-3 fragment having a length of 2.9 kb (hereinafter often referred to as "HG-3/EcoRI 2.9 kb fragment") is recovered from the melted gel by extracting 3 times with phenol and then 3 times with another extraction solvent, followed by precipitation with ethanol containing ammonium acetate. Thus, there is obtained 637 ng (yield: about 30%) of HG-3/EcoRI 2.9 kb fragment.

255 ng of the above -obtained fragment is ligated to 56.5 ng of EcoRI-cleaved pUC 13 [J. Messing, Methods in Enzymology, Vol. 101, 20 (1983)] using 2.5 units of T₄ ligase at 4° C. for 20 hours.

E. coli K 12 strain JM83 is transformed using the above-obtained ligation product. Specifically, E. coli K12 strain JM83 is cultured in LB medium until the optical density of the culture broth becomes 0.3 at 550 nm. 50 ml of the grown E. coli K12 strain JM83 culture is collected, washed with a 25 ml of 10 mM MOPS(pH7.0)-10mM RbCl, and resuspended into a 25 ml of 0.1M MOPS(pH6.5)-50 mM CaCl₂-10 mM RbCl. The suspension is cooled on ice for 30 min., centrifuged and resuspended in a mixture of 2 ml of 0.1M MOPS(pH6.5)-50 mM CaCl₂-10 mM RbCl and 30 μl of DMSO. To 203 μl of the suspension is added 10 μl of an aqueous ligation product solution containing 10 ng of the ligation product. The mixture is cooled on ice for 30 min. and then heated at 40° C. for 60 seconds. Immediately thereafter, 5 ml of LB broth prewarmed at 37° C. is added to the heated mixture, followed by incubation at 37° C. for one hour. The obtained culture broth is subjected to centrifugation and the supernatant is removed. An LB medium is added to the resulting cell pellet and then inoculated on an LB plate containing 30 μg/ml ampicillin and 40 μg/ml X-gal. Colonies containing E. coli K12 strain JM83 which have been transformed with the plasmids having the insert are white, while those containing E. coli K12 strain JM83 which have been transformed with plasmid only are blue. The obtained white colonies are inoculated again on LB plate containing 30 μg/ml ampicillin and 40 μg/ml X-gal for the purpose of confirmation.

From the above-obtained white colonies ten colonies (bacterial clones) are selected and screened by using a mini-prep technique.

Specifically, each colony is cultured overnight in LB medium containing 30 μg/ml ampicillin. The grown cells are collected and suspended in a solution containing 2 mg/ml lysozyme-50 mM glucose-10 mM EDTA-25 mM Tris HCl(pH8.0). The suspension is allowed to stand at room temperature for 5 minutes, followed by addition of 200 μl of 0.2 N NaOH-1% SDS. After slowly stirring, the suspension is allowed to stand at room temperature for 2 min. Thereafter, 150 μl of 3M sodium acetate (H5.2) is added, allowed to stand at −20° C. for 10 min., followed by centrifugation for 15 min. to recover the resulting supernatant. To the supernatant is added 900 μl of cold ethanol, followed by centrifugation for 5 min. to obtain the resulting precipitate. The obtained precipitate is washed with 70% ethanol and dried to get a plasmid DNA. In the above-mentioned method, ten plasmid DNAs are obtained.

Each plasmid DNA is dissolved in 10 mM Tris-0.1 mM EDTA(pH8.0), digested with EcoRI and subjected to electrophoresis for restriction analysis. The conditions for digestion and electrophoresis are as follows.

Digestion: plasmid DNA solution, one-fifth of the amount as prepared above; EcoRI, 3 units; 37° C.; 1.5 hr Electrophoresis: 1% agarose gel; 1×TAE; 120 V; 2 hr The above restriction analysis shows that eight of ten clones are positive. That is, the eight clones have 2.9 kb fragment. From the eight positive clones one clone is selected and designated as *E. coli* K12 strain JM83 (pHGE) (ATCC 39656).

Substantially the same procedures as in the above Step 2 are repeated to prepare 1.89 mg of pHGE DNA, except that *E. coli* K12 strain JM83 (pHGE) is used instead of *E. coli* harboring pB2-7 and pR18.

Step 10

(Subcloning of EcoRI-cleaved RG-1)

30 μg of RG-1 as prepared in the above Step 6 is digested with EcoRI. From the resulting fragment mixture the fragment having a length of about 3.5 kb is recovered in substantially the same manner as in the above step 9, except that the above prepared fragment mixture and 0.8% low melting agarose gel are used. There is obtained 1.0 μg of EcoRI-cleaved RG-1 fragment (about 3.5 kb). The above-obtained EcoRI-cleaved RG-1 fragment (3.5 kb) is ligated to EcoRI-digested pUC13 in substantially the same manner as in the above step 9, except that the above-obtained EcoRI-cleaved fragment (3.5 kb) is used instead of EcoRI-cleaved HG-3 fragment (2.9 kb).

The transformation of *E. coli* K12 strain JM83, screening of bacterial clones, digestion of clones and electrophoresis are effected in substantially the same manner as in the above Step 9, except that the above-obtained ligation product is used. The obtained clone is designated as *E. coli* K12 strain JM83 (pRGE) (ATCC 39655).

Substantially the same procedures as in the above Step 2 are repeated to prepare 1.70 mg of pRGE DNA, except that *E. coli* K12 strain JM83 (pRGE) is used instead of pB2-7 and pR-18.

Step 11

(Restriction enzyme analysis of pHGE plasmid DNA)

The restriction enzyme analysis of pHGE DNA as obtained in the above Step 9 is effected according to the method as described in Maniatis [Molecular Cloning, Cold Spring Harbor Laboratory, 98 (1982)].

The procedures and conditions used are as follows.
(1) Digestion of pHGE DNA with EcoRI: 18.6 μg pHGE DNA 64 units EcoRI 37° C., 2 hr
(2) Ethanol precipitation: precipitate
(3) Addition of distilled water to precipitate: Preparation of 1 μg/μl EcoRI-cleaved pHGE soln.
(4) Digestion with various restriction enzymes: 1 μg pHGE/EcoRI Restriction enzyme: 5 units PvuII, 5 units PvuII+10 units RsaI, 10 units RsaI, 4 units MstII, 3 units AvaI, 9 units PstI 37° C., 2 hr
(5) Electrophoresis: 2% Agarose gel, 1×TAE, 28 V, 14.5 hr
(6) Transfer to nitrocellulose filter: [see E. M. Southern, J. Mol. Biol., 98,503 (1975)]
(7) First pre-hybridization: 30 ml FDSS 42° C., 6 hr
(8) First hybridization: 5'-fragment ($5 \times 10^4$ cpm/ml) of pR18 (prepared in the above Step 4) 42° C., 14 hr
(9) Washing: 2×SSC—0.1% SDS at room temp. Immersion 10 min.×4 1×SSC—0.1% SDS at 50° C. Immersion 30 min×2
(10) Exposure: XAR-5(Eastman Kodak Company, U.S.A.), −80° C., 2 intensifying screens, 17.5 hrs
(11) Washing out: 0.5M NaOH—1.5M NaCl (Immersion: 1 min.) 0.5M Tris—1.5M NaCl (Immersion: 1 min.) 3×SSC (Immersion: 1 min.)
(12) Exposure: Effected in the same manner as in the above 10), except that exposure time is 19 hrs.
(13) Second pre-hybridization: In the same manner as in the above 7)
(14) Second hybridization: pB2-7 insert (prepared in the above Step (3), 42° C., 16.5 hrs
(15) Washing: In the same manner as in the above (9)
(16) Exposure: In the same manner as in the above (10), except that exposure time is 19.5 hrs.
(17) Washing Out: In the same manner as in the above (11)
(18) Exposure: In the same manner as in the above (10), except that the exposure time is 20 hrs.
(19) Third pre-hybridization: In the same manner as in the above (7).
(20) Third hybridization: 3'-fragment ($4.5 \times 10^5$ cpm/ml) of pR18 (prepared in the above Step 4), 42° C., 15 hr.
(21) Washing: In the same manner as in the above (9).
(22) Exposure: In the same manner as in the above (10).

Figure 4:
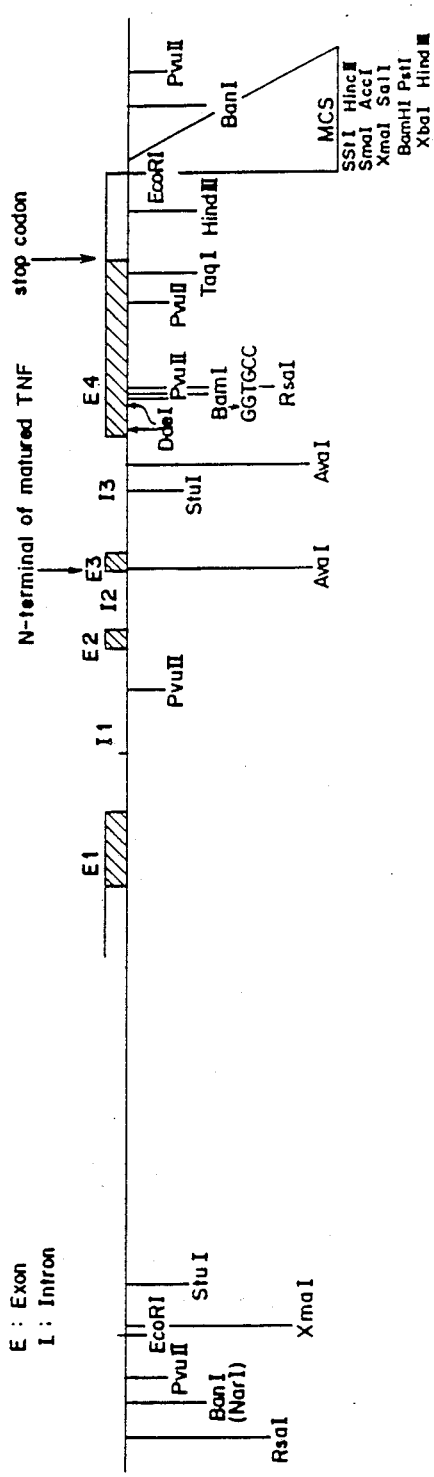
FIG. 4 illustrates the restriction map of the portion of a plasmid containing a gene for human physiologically active polypeptide of the present invention.

The results of the restriction enzyme analysis are shown in FIG. 4.

Step 12

(Restriction enzyme analysis of pRGE plasmid DNA)

Figure 5:
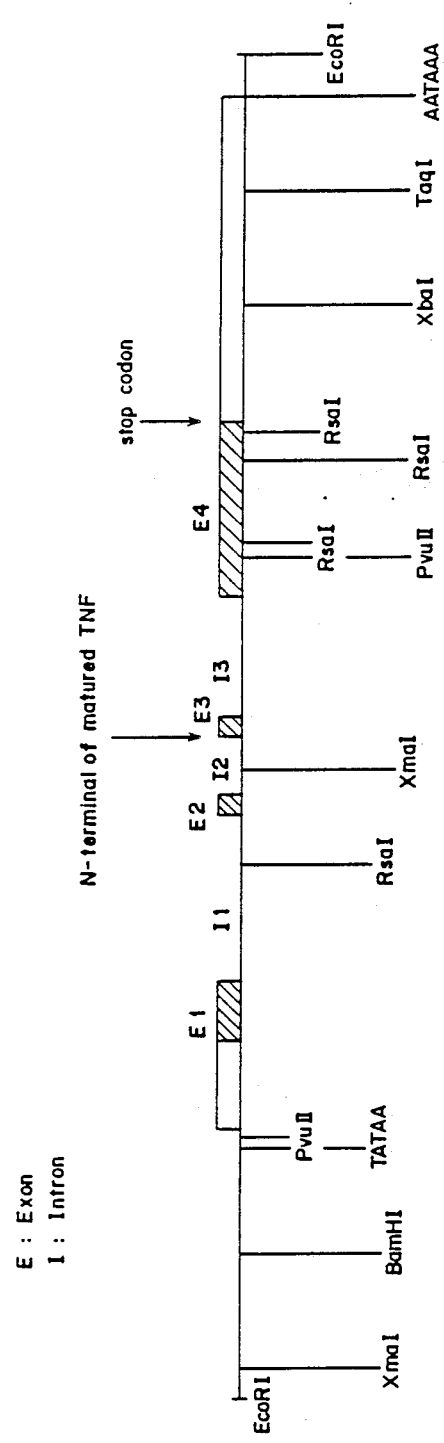
FIG. 5 illustrates the restriction map of the portion of a plasmid containing a gene for a conventional rabbit physiologically active polypeptide.

In substantially the same manner as in the above Step 11, the restriction enzyme analysis of pRGE plasmid DNA prepared in the above Step 10 is effected, except that pRGE plasmid DNA is used instead of pHGE plasmid DNA. The restriction map of pRGE DNA insert obtained is shown in FIG. 5.

Step 13

(Determination of base sequences of rabbit TNF gene and human TNF gene)

Substantially the same procedures as in the above Step 2 are repeated, except that *E. coli* K12 strain JM83 (pHGE) obtained in the above Step 9 and *E. coli* K12 strain JM83 (pRGE) obtained in the above Step 10 are used instead of *E. coli* K12 strain MC1061 having pB2-7 and *E. coli* K12 strain MC1061 having pR18. Thus, 150 μg of each of pRGE plasmid DNA and pHGE plasmid DNA is obtained.

The base sequences of pRGE and pHGE are determined according to the Maxam-Gilbert method [Maxam et al, Methods in Enzymology, Vol. 55, 490 (1980) published by Academic Press].

The base sequence of pR-18 determined in Referential Example 3 is compared with that of pRGE as determined above to elucidate the structure, including exon and intron, of rabbit TNF gene. The structure of pRGE DNA insert is shown in FIG. 5. Subsequently, the base sequence of pRGE is compared with that of pHGE to investigate the homology and consensus sequence around the boundary between intron and exon. Thus, the structure, including exon and intron, of human TNF gene is elucidated. The structure of human TNF gene is shown in FIG. 4.

The above-obtained base sequence coding for rabbit TNF and human TNF will be shown below. In the base sequences, the upper row shows the base sequence coding for rabbit TNF (R) and the lower row the base sequence coding for human TNF (H).

inserted into EcoRI fragment from the replicative form of M13mp9 phage. The M13mp9 phage is selected because it is especially suited for receiving sections of DNA. The product transfects to *E. coli* JM103 [BRL (Bethesda Research Laboratories, Inc., U.S.A.) User Manual/M13mp7 Cloning/'Dideoxy' sequencing, 1980]. The product is designated M13mp9-HGE.

| R | TCA | GCT | TCT | CGG | GCC | CTG | AGT | GAC | AAG | CCT | CTA | GCC | CAC | GTA | GTA |
|---|---|---|---|---|---|---|---|---|---|---|---|---|---|---|---|
| H | TCA | TCT | TCT | CGA | ACC | CCG | AGT | GAC | AAG | CCT | GTA | GCC | CAT | GTT | GTA |
| R | GCA | AAC | CCG | CAA | GTG | GAG | GGC | CAG | CTC | CAG | TGG | CTG | AGC | CAG | CGT |
| H | GCA | AAC | CCT | CAA | GCT | GAG | GGG | CAG | CTC | CAG | TGG | CTG | AAC | CGC | CGG |
| R | GCG | AAC | GCC | CTG | CTG | CGC | AAC | GGC | ATG | AAG | CTC | ACG | GAC | AAC | CAG |
| H | GCC | AAT | GCC | CTC | CTG | GCC | AAT | GGC | GTG | GAG | CTG | AGA | GAT | AAC | CAG |
| R | CTG | GTG | GTG | CCG | GCC | GAC | GGG | CTG | TAC | CTC | ATC | TAC | TCC | CAG | GTT |
| H | CTG | GTG | GTG | CCA | TCA | GAG | GGC | CTG | TAC | CTC | ATC | TAC | TCC | CAG | GTC |
| R | CTC | TTC | AGC | GGT | CAA | GGC | TGC | CGC | TCC | ... | TAC | GTG | CTC | CTC | ACT |
| H | CTC | TTC | AAG | GGC | CAA | GGC | TGC | CCC | TCC | ACC | CAT | GTG | CTC | CTC | ACC |
| R | CAC | ACT | GTC | AGC | CGC | TTC | GCC | GTC | TCC | TAC | CCG | AAC | AAG | GTC | AAC |
| H | CAC | ACC | ATC | AGC | CGC | ATC | GCC | GTC | TCC | TAC | CAG | ACC | AAG | GTC | AAC |
| R | CTC | CTC | TCT | GCC | ATC | AAG | AGC | CCC | TGC | CAC | CGG | GAG | ACC | CCC | GAG |
| H | CTC | CTC | TCT | GCC | ATC | AAG | AGC | CCC | TGC | CAG | AGG | GAG | ACC | CCA | GAG |
| R | GAG | GCT | GAG | CCC | ATG | GCC | TGG | TAC | GAG | CCC | ATC | TAC | CTG | GGC | GGC |
| H | GGG | GCT | GAG | GCC | AAG | CCC | TGG | TAT | GAG | CCC | ATC | TAT | CTG | GGA | GGG |
| R | GTC | TTC | CAG | TTG | GAG | AAG | GGT | GAC | CGG | CTC | AGC | ACC | GAG | GTC | AAC |
| H | GTC | TTC | CAG | CTG | GAG | AAG | GGT | GAC | CGA | CTC | AGC | GCT | GAG | ATC | AAT |
| R | CAG | CCT | GAG | TAC | CTG | GAC | CTT | GCC | GAG | TCC | GGG | CAG | GTC | TAC | TTT |
| H | CGG | CCC | GAC | TAT | CTC | GAC | TTT | GCC | GAG | TCT | GGG | CAG | GTC | TAC | TTT |
| R | GGG | ATC | ATT | GCC | CTG |
| H | GGG | ATC | ATT | GCC | CTG |

Note:
the symbol "..." means that this portion in the base sequence of the DNA coding for rabbit TNF is null and, therefore, two codons adjacent to this symbol at its both sides are directly connected.

Step 14
(Synthesis of oligodeoxynucleotides)

To a stainless steel 500 µl reaction vessel with stainless steel filters at each end is added 20 mg of a polystyrene resin to which a nucleoside (2.0 µM) is connected via a succinate linkage. The resin is treated with zinc bromide (1M) in dichloromethane isopropanol (85:15) to remove the dimethoxytrityl (DMT) protecting group, washed with dimethylformamide, pyridine, and acetonitrile, and dried with a stream of nitrogen. To the dried resin is added a solution of DMT-nucleotide (20 µM) and mesitylenesulfonylnitrotriazole (60 µM) in 200 µl pyridine. The coupling reaction is allowed to proceed at 45° C. for 20 minutes. This cycle of deprotection and coupling is repeated for successive nucleotides until the desired oligodeoxynucleotide is assembled on the resin. The resin is then treated to remove the oligodeoxynucleotide therefrom and purified as described by Ito, Ike, Ikuta, and Itakura (Nuc. Ac. Res. 10:1755 (1982)).

Thus, the following oligodeoxynucleotides are obtained.

(1) 5'-AATTCATGTCATCTTCTCGAACCC-CGAGTGACAA-3'
(2) 3'-GTACAGTAGAAGAGCTTGGGGCT-CACTGTTCGG-5'
(3) 5'-GCCTGTAGCCCATGTTGTAG-CAAACCCTCAAGC-3'
(4) 3'-ACATCGGGTACAACATCGTTTG-GGAGTTCGACT-5'

Step 15
(Construction of M13mp9-HGE containing the human minigene for TNF)

Plasmid pHGE (10 µg) is digested with EcoRI (20 units). After electrophoresis on a 1% low-melting agarose gel, the 2.9 kb fragment is eluted. This fragment is

Step 16
(Deletion of Intron 3, using M13mp9-HGE single strand DNA and Deleter E3-4)

The single strand DNA of M13mp9-HGE is prepared by the method of BRL User Manual/M13mp7 cloning/'Dideoxy' sequencing, 1980. Oligodeoxynucleotide (4) 3'-ACATCGGGTACAACATCGTTTG-GGAGTTCGACT-5' prepared in Step 14 is used as a deleter for the intron 3. The deleter for the intron 3 is designated "E3-4".

The deleter E3-4 has a base sequence which is complementary to the base sequence of the bases before (Exon 3) and after (Exon 4) the intron 3 which is to be deleted. Deletion of the intron 3 is effected, in accordance with the teaching of Wallace et al, Science 209:1396 (1980), as follows.

E3-4 (164 ng, 15 pmole) is phosphorylated using T4 kinase and ATP (3 mM) and added to the template M13mp9-HGE (1.65 µg, 0.5 pmole). The reaction mixture is heated at 65° C., cooled to room temperature for 5 minutes, and finally cooled in ice water. To dATP, dCTP, dGTP, dTTP and ATP (0.4 mM), is added Klenow fragment (5 units), T4 ligase (10 units) in Hin buffer [Wallace et al, Nuc. Ac. Res. 9; 3647 (1981)], 10 mM Tris HCl (pH 7.2), 2 mM MgCl², and 1 mM β-mercaptoethanol. The reaction mixture (final volume 50 ul) is incubated for 30 minutes at 4° C. and then for 30 minutes at room temperature. The DNA from the oligonucleotide-primed reaction is used to transfect *E. coli* JM103 in accordance with the procedure of BRL User Manual/M13mp7 cloning/'Dideoxy' sequencing, 1980. Plaques obtained in this way are picked to YT plates [J. H. Miller, p. 433, Experiments in Molecular Genetics, Cold Spring Harbor Laboratory (1972)]. The colonies obtained are hybridized at 55° C. for 2 hours with $^{32}$P-labelled E3-4. For this step, the deleter is used as a probe to identify sequences of DNA having the corresponding complementary base sequence after the intron has been deleted. Phage are isolated from those colonies which hybridize with the deleter.

The resultant phage are plated and plaques are picked to YT plates. The clones are allowed to hybridize at 55° C. for 2 hours with $^{32}$p-labelled E3-4. Positive clones are obtained and the phage DNA is sequenced to select those phage in which intron 3 is completely deleted. One such phage is designated mp9-HGEΔ 3-1.

Step 17

(Construction of pHTNF-lacUV5-2)

The replicative form of mp9-HGE Δ3-1 is digested with EcoRI. The EcoRI fragment is isolated and cloned to EcoRI-cleaved pBR327 to yield the plasmid pHGEΔ 3-1.

Figure 7:
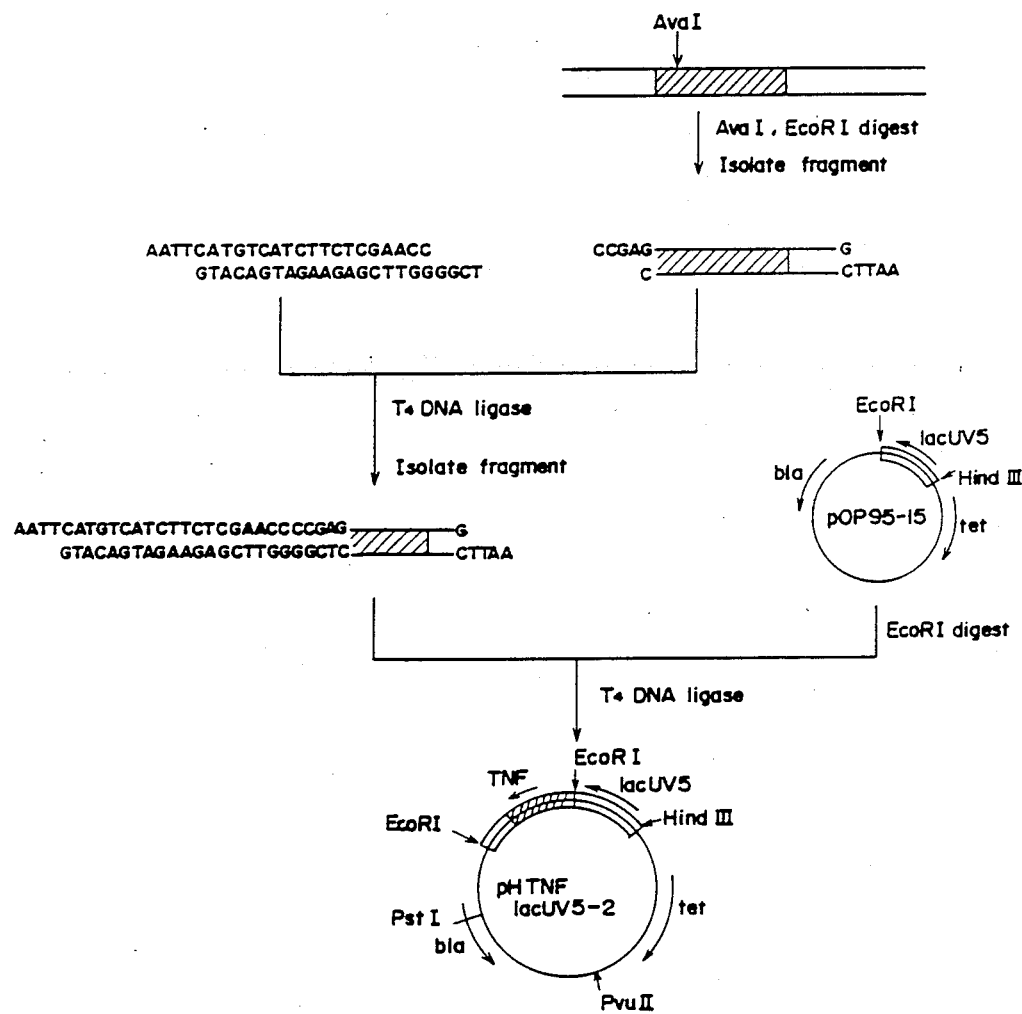
FIG. 7 illustrates the flow-sheet of the method for the preparation of another recombinant DNA (pHTNF-lacUV5-2) coding for the human physiologically active polypeptide of the present invention.

Construction of further plamids is carried out using plasmid pHGE Δ 3-1 in order to obtain such plasmid Δ 3-1 as will directly express TNF in *E. coli* using lac UV5 as a promoter. The procedures are illustratively shown in FIG. 7. First, 10 μg of plasmid pHGE Δ 3-1 is digested with 10 units of AvaI and EcoRI (manufactured and sold by Bethesda Research Laboratories, Inc., U.S.A.) at 37° C. for two hours and electrophoresed on a 4% by weight polyacrylamide gel to isolate fragments. About 1 μg of fragment is isolated from the gel by electroelution. In the same manner as in Step 14, two oligodeoxynucleotides shown in FIG. 7, namely 5'-AATTCATGTCATCTTCTCGAACC-3' and 5'-TCGGGGTTCGAGAAGATGACATG-3' are synthesized. Then, each 5' end of the two oligodeoxynucleotides (about 100 pmole) is phosphorylated using T4 polynucleotide kinase in accordance with the method described in Literature (3), page 122. After completion of the reaction, the reaction mixture is extracted with phenol and then with chloroform. Then the so-obtained synthetic oligomers are mixed with 0.5 μg of the previously obtained AvaI-EcoRI fragment from plasmid pHGE Δ 3-1 and ethanol precipitated. These fragments are ligated at 4° C. overnight using 10 units of T4 ligase in accordance with the procedure described in Literature (1), page 37. After completion of the reaction, the mixture is ethanol precipitated, followed by electrophoresis effected on a 4% by weight polyacrylamide gel to recover fragment by electroelution.

In accordance with the procedure described in F. Fuller, "Gene", 19, pp. 42-54 (1982), plasmid pOP95-15 is prepared.

One μg of pOP 95-15 is digested with EcoRI and extracted with phenol and then with chloroform, followed by ethanol precipitation to obtain a vector. Using T4 DNA ligase, 0.5 μg of the obtained vector is ligated with the above-obtained fragment. In accordance with the procedure described in Literature (4), page 20, *E. coli* JM101 (ATCC 33876) is transformed using the above-obtained vector and cultivated on an agar medium containing 1 mM of IPTG and 0.004 w/v % x-gal to obtain about 100 white colonies.

Plasmid DNA is prepared from these transformants and digested with EcoRI to identify those plasmids containing the intended EcoRI fragment. In order to examine the direction of insertion, those plasmids are digested with PvuII and PstI and electrophoresed on a 1.5% by weight agarose gel to select plasmids yielding fragments of about 1280 base pairs and about 2600 base pairs indicating that the direction of transcription of the lac UV5 promoter is in agreement with those of the oligodeoxynucleotides coding for TNF.

Base sequence analysis shows that these 2 plasmids have the same sequence and that the lac UV5 promotoer, the synthesized oligodeoxynucleotide and DNA are properly combined with each other. The obtained plasmid is designated pHTNF-lacUV5-2.

*E. coli* containing pHTNF-lacUV5-2 is cultured in a conventional nutrient medium. Bioassay of the product for TNF activity indicates the same activity which is obtained with a plasmid pTNF-lacUV5-1 containing the rabbit TNF gene under control of the lac promoter.

EXAMPLE 2

Figure 6:
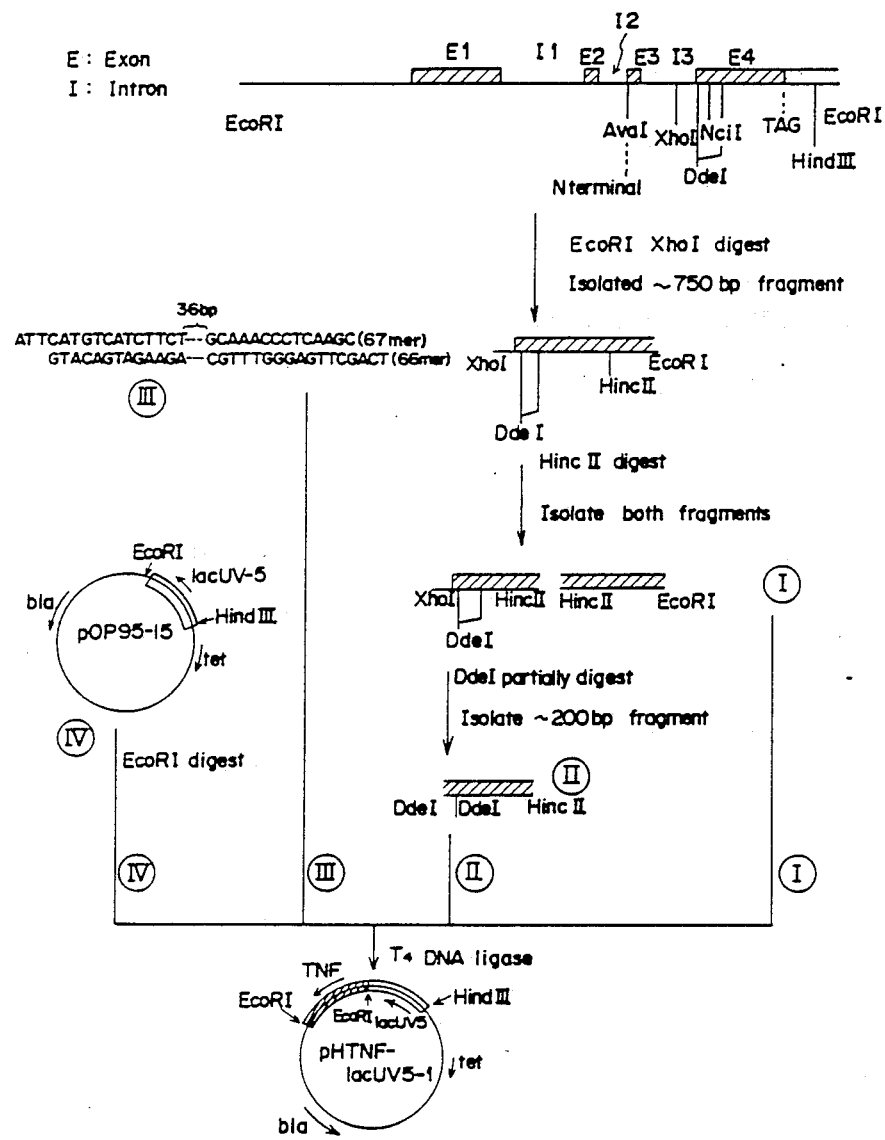
FIG. 6 illustrates the flow-sheet of the method for the preparation of a recombinant DNA (pHTNF-lacUV5-1) coding for a human physiologically active polypeptide of the present invention.

Using the plasmid pHGE and oligodeoxynucleotides 1 to 4) obtained by the procedure described in Steps 1 to 14 of Example 1 pHTNF-lacUV5-1 is prepared in accordance with the procedure illustrated in FIG. 6

It will be understood that the novel microorganisms and cell cultures which form a part of the present invention are important and novel due to their ability to produce human TNF. Therefore, in addition to the transformed microorganisms and cell cultures prepared according to the above discussion, the present invention further includes mutants and variants thereof which are also capable of exhibiting the important activity in producing TNF.

The microorganisms and the novel plasmids were placed on deposit in the American Type Culture Collection in Rockville, Md., U.S.A. on Apr. 6, 1984 by depositing samples of the microorganisms containing the plasmids. The microorganism *E. coli* k-12 strain JM83 (pRGE) was given the ATCC accession number 39655. The microorganism *E. coli* k-12 strain JM83 (pHGE) was given the ATCC accession number 39656.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An isolated physiologically active human tumor necrosis factor polypeptide comprising an amino acid sequence represented by the following formula:

Ser Ser Ser Arg Thr Pro Ser Asp Lys Pro Val Ala His Val Val
Ala Asn Pro Gln Ala Glu Gly Gln Leu Gln Trp Leu Asn Arg
Arg Ala Asn Ala Leu Leu Ala Asn Gly Val Glu Leu Arg Asp
Asn Gln Leu Val Val Pro Ser Glu Gly Leu Tyr Leu Ile Tyr
Ser Gln Val Leu Phe Lys Gly Gln Gly Cys Pro Ser Thr His
Val Leu Leu Thr His Thr Ile Ser Arg Ile Ala Val Ser Tyr
Gln Thr Lys Val Asn Leu Leu Ser Ala Ile Lys Ser Pro Cys Gln
Arg Glu Thr Pro Glu Gly Ala Glu Ala Lys Pro Trp Tyr Glu
Pro Ile Tyr Leu Gly Gly Val Phe Gln Leu Glu Lys Gly Asp
Arg Leu Ser Ala Glu Ile Asn Arg Pro Asp Tyr Leu Asp Phe
Ala Glu Ser Gly Gln Val Tyr Phe Gly Ile Ile Ala Leu wherein Gln stands for a glutamine residue, Asp an aspartic acid residue, Pro a proline residue, Tyr a tyrosine residue, Val a valine residue, Lys a lysine residue, Glu a glutamic acid residue, Ala an alanine residue, Asn an asparagine residue, Leu a leucine residue, Phe a phenylalanine residue, Gly a glycine residue, His a histidine residue, Ser a serine residue, Thr a threonine residue, Ile an isoleucine residue, Trp a tryptophan residue, Arg an arginine residue, and Cys a cysteine residue, or a variant of said polypeptide having all of the activity of human tumor necrosis factor.

2. A composition of matter consisting essentially of a physiologically active human tumor necrosis factor polypeptide comprising an amino acid sequence represented by the formula:

Ser Ser Ser Arg Thr Pro Ser Asp Lys Pro Val Ala His Val Val
Ala Asn Pro Gln Ala Glu Gly Gln Leu Gln Trp Leu Asn Arg
Arg Ala Asn Ala Leu Leu Ala Asn Gly Val Glu Leu Arg Asp
Asn Gln Leu Val Val Pro Ser Glu Gly Leu Tyr Leu Ile Tyr
Ser Gln Val Leu Phe Lys Gly Gln Gly Cys Pro Ser Thr His
Val Leu Leu Thr His Thr Ile Ser Arg Ile Ala Val Ser Tyr
Gln Thr Lys Val Asn Leu Leu Ser Ala Ile Lys Ser Pro Cys Gln
Arg Glu Thr Pro Glu Gly Ala Glu Ala Lys Pro Trp Tyr Glu
Pro Ile Tyr Leu Gly Gly Val Phe Gln Leu Glu Lys Gly Asp
Arg Leu Ser Ala Glu Ile Asn Arg Pro Asp Tyr Leu Asp Phe
Ala Glu Ser Gly Gln Val Tyr Phe Gly Ile Ile Ala Leu wherein Gln stands for glutamine residue, Asp an aspartic acid residue, Pro a proline residue, Tyr a tyrosine residue, Val a valine residue, Lys a lysine residue, Glu a glutamic acid residue, Ala an alanine residue, Asn an asparagine residue, Leu a leucine residue, Phe a phenylalanine residue, Gly a glycine residue, His a histidine residue, Ser a serine residue, Thr a threonine residue, Ile an isoleucine residue, Trp a tryptophan residue, Arg an arginine residue, and Cys a cysteine residue, or a variant of said polypeptide having all of the activity of human tumor necrosis factor.

3. A composition of matter comprising an effective anti-tumor amount of a physiologically active human tumor necrosis factor polypeptide comprising an amino acid sequence represented by the formula:

Ser Ser Ser Arg Thr Pro Ser Asp Lys Pro Val Ala His Val Val
Ala Asn Pro Gln Ala Glu Gly Gln Leu Gln Trp Leu Asn Arg
Arg Ala Asn Ala Leu Leu Ala Asn Gly Val Glu Leu Arg Asp
Asn Gln Leu Val Val Pro Ser Glu Gly Leu Tyr Leu Ile Tyr
Ser Gln Val Leu Phe Lys Gly Gln Gly Cys Pro Ser Thr His
Val Leu Leu Thr His Thr Ile Ser Arg Ile Ala Val Ser Tyr
Gln Thr Lys Val Asn Leu Leu Ser Ala Ile Lys Ser Pro Cys Gln
Arg Glu Thr Pro Glu Gly Ala Glu Ala Lys Pro Trp Tyr Glu
Pro Ile Tyr Leu Gly Gly Val Phe Gln Leu Glu Lys Gly Asp
Arg Leu Ser Ala Glu Ile Asn Arg Pro Asp Tyr Leu Asp Phe
Ala Glu Ser Gly Gln Val Tyr Phe Gly Ile Ile Ala Leu wherein Gln stands for a glutamine residue, Asp an aspartic acid residue, Pro a proline residue, Tyr a tyrosine residue, Val a valine residue, Lys a lysine residue, Glu a glutamic acid residue, Ala an alanine residue, Asn an asparagine residue, Leu a leucine residue, Phe a phenylalanine residue, Gly a glycine residue, His a histidine residue, Ser a serine residue, Thr a threonine residue, Ile an isoleucine residue, Trp a tryptophan residue, Arg an arginine residue, and Cys a cysteine residue, or a variant of said polypeptide having all of the activity of human tumor necrosis factor, wherein said human polypeptide or variant thereof is derived from a microorganism or cell transformed with a gene for said polypeptide.

4. The composition of claim 3, which is prepared by cultivating said microorganism, recovering said polypeptide and purifying said polypeptide.

5. The composition of claim 4, wherein said polypeptide consists of an amino acid sequence represented by the following formula:

Ser Ser Ser Arg Thr Pro Ser Asp Lys Pro
Val Ala His Val Val Ala Asn Pro Gln Ala
Glu Gly Gln Leu Gln Trp Leu Asn Arg Arg
Ala Asn Ala Leu Leu Ala Asn Gly Val Glu
Leu Arg Asp Asn Gln Leu Val Val Pro Ser
Glu Gly Leu Tyr Leu Ile Tyr Ser Gln Val
Leu Phe Lys Gly Gln Gly Cys Pro Ser Thr
His Val Leu Leu Thr His Thr Ile Ser Arg
Ile Ala Val Ser Tyr Gln Thr Lys Val Asn
Leu Leu Ser Ala Ile Lys Ser Pro Cys Gln
Arg Glu Thr Pro Glu Gly Ala Glu Ala Lys
Pro Trp Tyr Glu Pro Ile Tyr Leu Gly Gly
Val Phe Gln Leu Glu Lys Gly Asp Arg Leu
Ser Ala Glu Ile Asn Arg Pro Asp Tyr Leu
Asp Phe Ala Glu Ser Gly Gln Val Tyr Phe
Gly Ile Ile Ala Leu.

6. A method for producing a physiologically active human tumor necrosis factor polypeptide comprising an amino acid sequence represented by the following formula:

Ser Ser Ser Arg Thr Pro Ser Asp Lys Pro Val Ala His Val Val
Ala Asn Pro Gln Ala Glu Gly Gln Leu Gln Trp Leu Asn Arg
Arg Ala Asn Ala Leu Leu Ala Asn Gly Val Glu Leu Arg Asp
Asn Gln Leu Val Val Pro Ser Glu Gly Leu Tyr Leu Ile Tyr
Ser Gln Val Leu Phe Lys Gly Gln Gly Cys Pro Ser Thr His
Val Leu Leu Thr His Thr Ile Ser Arg Ile Ala Val Ser Tyr
Gln Thr Lys Val Asn Leu Leu Ser Ala Ile Lys Ser Pro Cys Gln
Arg Glu Thr Pro Glu Gly Ala Glu Ala Lys Pro Trp Tyr Glu
Pro Ile Tyr Leu Gly Gly Val Phe Gln Leu Glu Lys Gly Asp
Arg Leu Ser Ala Glu Ile Asn Arg Pro Asp Tyr Leu Asp Phe
Ala Glu Ser Gly Gln Val Tyr Phe Gly Ile Ile Ala Leu wherein Gln stands for a glutamine residue, Asp an aspartic acid residue, Pro a proline residue, Tyr a tyrosine residue, Val a valine residue, Lys a lysine residue, Glu a glutamic acid residue, Ala an alanine residue, Asn an asparagine residue, Leu a leucine residue, Phe a phenylalanine residue, Gly a glycine residue, His a histidine residue, Ser a serine residue, Thr a threonine residue, Ile an isoleucine residue, Trp a tryptophan residue, Arg an arginine residue, and Cys a cysteine residue or a variant of said polypeptide having all of the activity of human tumor necrosis factor which comprises:

(a) ligating a deoxyribonucleic acid comprising a base sequence coding for said physiologically active polypeptide to a replicable expression vehicle to obtain a replicable recombinant DNA comprising said deoxyribonucleic acid and said replicable expression vehicle;

(b) transforming cells of a microorganism or cell culture with said replicable recombinant DNA to form transformants;

(c) selecting said transformants from parent cells of the microorganism or cell culture;

(d) incubating said transformants, causing said transformants to express said deoxyribonucleic acid and produce a physiologically active human polypeptide; and (e) isolating said human physiologically active polypeptide from the incubated transformants.

7. The method of claim 6, further comprising the step of purifying the isolated polypeptide.

8. An isolated deoxyribonucleic acid capable of coding for a human tumor necrosis factor polypeptide having tumor necrosis factor activity comprising at least one base sequence selected from the group consisting of a base sequence represented by the following formula and a base sequence complementary to said base sequence:

TCA TCT TCT CGA ACC CCG AGT GAC

37

-continued
```
                AAG CCT GTA GCC CAT GTT GTA
GCA AAC CCT CAA GCT GAG GGG CAG
                CTC CAG TGG CTG AAC CGC CGG
GCC AAT GCC CTC CTG GCC AAT GGC
                GTG GAG CTG AGA GAT AAC CAG
CTG GTG GTG CCA TCA GAG GGC CTG
                TAC CTC ATC TAC TCC CAG GTC
CTC TTC AAG GGC CAA GGC TGC CCC
                TCC ACC CAT GTG CTC CTC ACC
CAC ACC ATC AGC CGC ATC GCC GTC
                TCC TAC CAG ACC AAG GTC AAC
CTC CTC TCT GCC ATC AAG AGC CCC
                TGC CAG AGG GAG ACC CCA GAG
GGG GCT GAG GCC AAG CCC TGG TAT
                GAG CCC ATC TAT CTG GGA GGG
GTC TTC CAG CTG GAG AAG GGT GAC
                CGA CTC AGC GCT GAG ATC AAT
CGG CCC GAC TAT CTC GAC TTT GCC
                GAG TCT GGG CAG GTC TAC TTT
GGG ATC ATT GCC CTG
``` wherein A stands for a deoxyadenylic acid residue, G a deoxyguanylic acid residue, C a deoxycytidylic acid residue and T a thymidylic acid residue and wherein the left end and right end of said formula represent the 5'-hydroxyl group side and 3'-hydroxyl group side, respectively, or comprising a base sequence which is obtained by substituting at least one base of said base sequence in accordance with the degeneracy of the Genetic Code, or a base sequence which codes for a variant of said human polypeptide having all of the activity of human tumor necrosis factor.

9. A replicable recombinant DNA which comprises a replicable expression vehicle and a deoxyribonucleic acid capable of coding for a human tumor necrosis factor polypeptide having tumor necrosis factor activity comprising at least one base sequence selected from the group consisting of a base sequence represented by the following formula and a base sequence complementary to said base sequence:

```
TCA TCT TCT CGA ACC CCG AGT GAC
                AAG CCT GTA GCC CAT GTT GTA
GCA AAC CCT CAA GCT GAG GGG CAG
                CTC CAG TGG CTG AAC CGC CGG
GCC AAT GCC CTC CTG GCC AAT GGC
                GTG GAG CTG AGA GAT AAC CAG
CTG GTG GTG CCA TCA GAG GGC CTG
                TAC CTC ATC TAC TCC CAG GTC
CTC TTC AAG GGC CAA GGC TGC CCC
                TCC ACC CAT GTG CTC CTC ACC
CAC ACC ATC AGC CGC ATC GCC GTC
                TCC TAC CAG ACC AAG GTC AAC
CTC CTC TCT GCC ATC AAG AGC CCC
                TGC CAG AGG GAG ACC CCA GAG
GGG GCT GAG GCC AAG CCC TGG TAT
                GAG CCC ATC TAT CTG GGA GGG
GTC TTC CAG CTG GAG AAG GGT GAC
                CGA CTC AGC GCT GAG ATC AAT
CGG CCC GAC TAT CTC GAC TTT GCC
                GAG TCT GGG CAG GTC TAC TTT
GGG ATC ATT GCC CTG
``` wherein A stands for deoxyadenylic acid residue, G a deoxyguanylic acid residue, C a deoxycytidylic acid residue and T a thymidylic acid residue and wherein the left end and right end of said formula represent the 5'-hydroxyl group side and 3'-hydroxyl group side, respectively, or comprising a base sequence which is obtained by substituting at least one base of said base sequence in accordance with the degeneracy of the Genetic Code, or a base sequence which codes for a variant of said human polypeptide having all of the activity of human tumor necrosis factor.

38

10. A microorganism or cell culture transformed with a replicable recombinant DNA which comprises a replicable expression vehicle and a deoxyribonucleic acid capable of coding for a human tumor necrosis factor polypeptide having tumor necrosis factor activity comprising at least one base sequence selected from the group consisting of a base sequence represented by the following formula and a base sequence complementary to said base sequence:

```
TCA TCT TCT CGA ACC CCG AGT GAC
                AAG CCT GTA GCC CAT GTT GTA
GCA AAC CCT CAA GCT GAG GGG CAG
                CTC CAG TGG CTG AAC CGC CGG
GCC AAT GCC CTC CTG GCC AAT GGC
                GTG GAG CTG AGA GAT AAC CAG
CTG GTG GTG CCA TCA GAG GGC CTG
                TAC CTC ATC TAC TCC CAG GTC
CTC TTC AAG GGC CAA GGC TGC CCC
                TCC ACC CAT GTG CTC CTC ACC
CAC ACC ATC AGC CGC ATC GCC GTC
                TCC TAC CAG ACC AAG GTC AAC
CTC CTC TCT GCC ATC AAG AGC CCC
                TGC CAG AGG GAG ACC CCA GAG
GGG GCT GAG GCC AAG CCC TGG TAT
                GAG CCC ATC TAT CTG GGA GGG
GTC TTC CAG CTG GAG AAG GGT GAC
                CGA CTC AGC GCT GAG ATC AAT
CGG CCC GAC TAT CTC GAC TTT GCC
                GAG TCT GGG CAG GTC TAC TTT
GGG ATC ATT GCC CTG
``` wherein A stands for a deoxyadenylic acid residue, G a deoxyguanylic acid residue, C a deoxycytidylic acid residue and T a thymidylic acid residue and wherein the left end and right end of said formula represent the 5'-hydroxyl group side and 3'-hydroxyl group side, respectively, or comprising a base sequence which is obtained by substituting at least one base of said base sequence in accordance with the degeneracy of the Genetic Code, or a base sequence which codes for a variant of said human polypeptide having all of the activity of human tumor necrosis factor.

11. A microorganism transformed with a replicable recombinant DNA which comprises a replicable expression vehicle and a deoxyribonucleic acid capable of coding for a human tumor necrosis factor polypeptide having tumor necrosis factor activity comprising at least one base sequence selected from the group consisting of a base sequence represented by the following formula and a base sequence complementary to said base sequence:

```
TCA TCT TCT CGA ACC CCG AGT GAC
                AAG CCT GTA GCC CAT GTT GTA
GCA AAC CCT CAA GCT GAG GGG CAG
                CTC CAG TGG CTG AAC CGC CGG
GCC AAT GCC CTC CTG GCC AAT GGC
                GTG GAG CTG AGA GAT AAC CAG
CTG GTG GTG CCA TCA GAG GGC CTG
                TAC CTC ATC TAC TCC CAG GTC
CTC TTC AAG GGC CAA GGC TGC CCC
                TCC ACC CAT GTG CTC CTC ACC
CAC ACC ATC AGC CGC ATC GCC GTC
                TCC TAC CAG ACC AAG GTC AAC
CTC CTC TCT GCC ATC AAG AGC CCC
                TGC CAG AGG GAG ACC CCA GAG
GGG GCT GAG GCC AAG CCC TGG TAT
                GAG CCC ATC TAT CTG GGA GGG
GTC TTC CAG CTG GAG AAG GGT GAC
                CGA CTC AGC GCT GAG ATC AAT
CGG CCC GAC TAT CTC GAC TTT GCC
                GAG TCT GGG CAG GTC TAC TTT
GGG ATC ATT GCC CTG
``` wherein A stands for a deoxyadenylic acid residue, G a deoxyguanylic acid residue, C a deoxycytidylic acid residue and T a thymidylic acid residue and wherein the left end and right end of said formula represent the 5'-hydroxyl group side and 3'-hydroxyl group side, respectively, or comprising a base sequence which is obtained by substituting at least one base of said base sequence in accordance with the degeneracy of the Genetic Code or a base sequence which codes for a variant of said human polypeptide having all of the activity of human tumor necrosis factor.

12. The transformed microorganism of claim 11, wherein said microorganism is a bacterium.

13. The transformed microorganism of claim 12, wherein said bacterium is *Escherichia coli*.

14. The transformed microorganism of claim 11, which is capable of producing a human tumor necrosis factor polypeptide consisting of an amino acid sequence of the formula:

TCA TCT TCT CGA ACC CCG AGT GAC
　　　　　　　AAG CCT GTA GCC CAT GTT GTA
GCA AAC CCT CAA GCT GAG GGG CAG
　　　　　　　CTC CAG TGG CTG AAC CGC CGG
GCC AAT GCC CTC CTG GCC AAT GGC
　　　　　　　GTG GAG CTG AGA GAT AAC CAG
CTG GTG GTG CCA TCA GAG GGC CTG
　　　　　　　TAC CTC ATC TAC TCC CAG GTC
CTC TTC AAG GGC CAA GGC TGC CCC
　　　　　　　TCC ACC CAT GTG CTC CTC ACC
CAC ACC ATC AGC CGC ATC GCC GTC
　　　　　　　TCC TAC CAG ACC AAG GTC AAC
CTC CTC TCT GCC ATC AAG AGC CCC
　　　　　　　TGC CAG AGG GAG ACC CCA GAG
GGG GCT GAG GCC AAG CCC TGG TAT
　　　　　　　GAG CCC ATC TAT CTG GGA GGG
GTC TTC CAG CTG GAG AAG GGT GAC
　　　　　　　CGA CTC AGC GCT GAG ATC AAT
CGG CCC GAC TAT CTC GAC TTT GCC
　　　　　　　GAG TCT GGG CAG GTC TAC TTT
GGG ATC ATT GCC CTG wherein Gln stands for a glutamine residue, Asp an aspartic acid residue, Pro a proline residue, Tyr a tyrosine residue, Val a valine residue, Lys a lysine residue, Glu a glutamic acid residue, Ala an alanine residue, Asn an asparagine residue, Leu a leucine residue, Phe a phenylalanine residue, Gly a glycine residue, His a histidine residue, Ser a serine residue, Thr a threonine residue, Ile an isoleucine residue, Trp a tryptophan residue, Arg an arginine residue, and Cys a cysteine residue.

15. The transformed microorganism of claim 13, wherein said *Escherichia coli* is *Escherichia coli* K-12.

16. The transformed microorganism of claim 11, wherein said microorganism is a bacterium and said replicable expression vehicle is a plasmid.

17. The transformed microorganism of claim 16, wherein said bacterium is *Escherichia coli*.

18. A pharmaceutical composition comprising:
an effective anti-tumor or anti-viral amount of a physiologically active human tumor necrosis factor polypeptide comprising an amino acid sequence represented by the following formula:

Ser Ser Ser Arg Thr Pro Ser Asp Lys Pro Val Ala His Val Val
Ala Asn Pro Gln Ala Glu Gly Gln Leu Gln Trp Leu Asn Arg
Arg Ala Asn Ala Leu Leu Ala Asn Gly Val Glu Leu Arg Asp
Asn Gln Leu Val Val Pro Ser Glu Gly Leu Tyr Leu Ile Tyr
Ser Gln Val Leu Phe Lys Gly Gln Gly Cys Pro Ser Thr His
Val Leu Leu Thr His Thr Ile Ser Arg Ile Ala Val Ser Tyr
Gln Thr Lys Val Asn Leu Leu Ser Ala Ile Lys Ser Pro Cys Gln
Arg Glu Thr Pro Glu Gly Ala Glu Ala Lys Pro Trp Tyr Glu
Pro Ile Tyr Leu Gly Gly Val Phe Gln Leu Glu Lys Gly Asp
Arg Leu Ser Ala Glu Ile Asn Arg Pro Asp Tyr Leu Asp Phe
Ala Glu Ser Gly Gln Val Tyr Phe Gly Ile Ile Ala Leu wherein Gln stands for a glutamine residue, Asp an aspartic acid residue, Pro a proline residue, Tyr a tyrosine residue, Val a valine residue, Lys a lysine residue, Glu a glutamic acid residue, Ala an alanine residue, Asn an asparagine residue, Leu a leucine residue, Phe a phenylalanine residue, Gly a glycine residue, His a histidine residue, Ser a serine residue, Thr a threonine residue, Ile an isoleucine residue, Trp a tryptophan residue, Arg an arginine residue, and Cys a cysteine residue, or a variant of said polypeptide having all of the activity of human tumor necrosis factor; and
at least one pharmaceutically acceptable carrier, diluent or excipient.

19. The pharmaceutical composition of claim 18, wherein said polypeptide comprises an amino acid sequence represented by the following formula:

Ser Ser Ser Arg Thr Pro Ser Asp Lys Pro
Val Ala His Val Val Ala Asn Pro Gln Ala
Glu Gly Gln Leu Gln Trp Leu Asn Arg Arg
Ala Asn Ala Leu Leu Ala Asn Gly Val Glu
Leu Arg Aap Asn Gln Leu Val Val Pro Ser
Glu Gly Leu Tyr Leu Ile Tyr Ser Gln Val
Leu Phe Lys Gly Gln Gly Cys Pro Ser Thr
His Val Leu Leu Thr His Thr Ile Ser Arg
Ile Ala Val Ser Tyr Gln Thr Lys Val Asn
Leu Leu Ser Ala Ile Lys Ser Pro Cys Gln
Arg Glu Thr Pro Glu Gly Ala Glu Ala Lys
Pro Trp Tyr Glu Pro Ile Tyr Leu Gly Gly
Val Phe Gln Leu Glu Lys Gly Asp Arg Leu
Ser Ala Glu Ile Asn Arg Pro Asp Tyr Leu
Asp Phe Ala Glu Ser Gly Gln Val Tyr Phe
Gly Ile Ile Ala Leu.

20. The pharmaceutical composition of claim 19, wherein said polypeptide consists of an amino acid sequence represented by the following formula:

Ser Ser Ser Arg Thr Pro Ser Asp Lys Pro
Val Ala His Val Val Ala Asn Pro Gln Ala
Glu Gly Gln Leu Gln Trp Leu Asn Arg Arg
Ala Asn Ala Leu Leu Ala Asn Gly Val Glu
Leu Arg Aap Asn Gln Leu Val Val Pro Ser
Glu Gly Leu Tyr Leu Ile Tyr Ser Gln Val
Leu Phe Lys Gly Gln Gly Cys Pro Ser Thr
His Val Leu Leu Thr His Thr Ile Ser Arg
Ile Ala Val Ser Tyr Gln Thr Lys Val Asn
Leu Leu Ser Ala Ile Lys Ser Pro Cys Gln
Arg Glu Thr Pro Glu Gly Ala Glu Ala Lys
Pro Trp Tyr Glu Pro Ile Tyr Leu Gly Gly
Val Phe Gln Leu Glu Lys Gly Asp Arg Leu
Ser Ala Glu Ile Asn Arg Pro Asp Tyr Leu
Asp Phe Ala Glu Ser Gly Gln Val Tyr Phe
Gly Ile Ile Ala Leu.

21. The pharmaceutical composition of claim 19, which is a pharmaceutically acceptable, injectable solution.

22. The pharmaceutical composition of claim 20, which is a pharmaceutically acceptable, injectable solution.

23. The pharmaceutical composition of claim 20, which is a pharmaceutically acceptable, injectable solution.

24. A method for treating tumors which comprises administering to a host an effective anti-tumor amount of a purified physiologically active human tumor necrosis factor polypeptide comprising an amino acid sequence represented by the following formula:

```
Ser Ser Ser Arg Thr Pro Ser Asp Lys Pro Val Ala His Val Val
Ala Asn Pro Gln Ala Glu Gly Gln Leu Gln Trp Leu Asn Arg
Arg Ala Asn Ala Leu Leu Ala Asn Gly Val Glu Leu Arg Asp
Asn Gln Leu Val Val Pro Ser Glu Gly Leu Tyr Leu Ile Tyr
Ser Gln Val Leu Phe Lys Gly Gln Gly Cys Pro Ser Thr His
Val Leu Leu Thr His Thr Ile Ser Arg Ile Ala Val Ser Tyr
Gln Thr Lys Val Asn Leu Leu Ser Ala Ile Lys Ser Pro Cys Gln
Arg Glu Thr Pro Glu Gly Ala Glu Ala Lys Pro Trp Tyr Glu
Pro Ile Tyr Leu Gly Gly Val Phe Gln Leu Glu Lys Gly Asp
Arg Leu Ser Ala Glu Ile Asn Arg Pro Asp Tyr Leu Asp Phe
Ala Glu Ser Gly Gln Val Tyr Phe Gly Ile Ile Ala Leu
``` wherein Gln stands for a glutamine residue, Asp an aspartic acid residue, Pro a proline residue, Tyr a tyrosine residue, Val a valine residue, Lys a lysine residue, Glu a glutamic acid residue, Ala an alanine residue, Asn an asparagine residue, Leu a leucine residue, Phe a phenylalanine residue, Gly a glycine residue, His a histidine residue, Ser a serine residue, Thr a threonine residue, Ile an isoleucine residue, Trp a tryptophan residue, Arg an arginine residue, and Cys a cysteine residue, or a variant of said polypeptide having all of the activity of human tumor necrosis factor.

25. The method of claim 24, wherein said polypeptide comprises an amino acid sequence represented by the following formula:

```
Ser Ser Ser Arg Thr Pro Ser Asp Lys Pro
Val Ala His Val Val Ala Asn Pro Gln Ala
Glu Gly Gln Leu Gln Trp Leu Asn Arg Arg
Ala Asn Ala Leu Leu Ala Asn Gly Val Glu
Leu Arg Asp Asn Gln Leu Val Val Pro Ser
Glu Gly Leu Tyr Leu Ile Tyr Ser Gln Val
Leu Phe Lys Gly Gln Gly Cys Pro Ser Thr
His Val Leu Leu Thr His Thr Ile Ser Arg
Ile Ala Val Ser Tyr Gln Thr Lys Val Asn
Leu Leu Ser Ala Ile Lys Ser Pro Cys Gln
Arg Glu Thr Pro Glu Gly Ala Glu Ala Lys
Pro Trp Tyr Glu Pro Ile Tyr Leu Gly Gly
Val Phe Gln Leu Glu Lys Gly Asp Arg Leu
Ser Ala Glu Ile Asn Arg Pro Asp Tyr Leu
Asp Phe Ala Glu Ser Gly Gln Val Tyr Phe
Gly Ile Ile Ala Leu.
```

26. The method of claim 24, wherein said polypeptide consists of an amino acid sequence represented by the following formula:

```
Ser Ser Ser Arg Thr Pro Ser Asp Lys Pro
Val Ala His Val Val Ala Asn Pro Gln Ala
Glu Gly Gln Leu Gln Trp Leu Asn Arg Arg
Ala Asn Ala Leu Leu Ala Asn Gly Val Glu
Leu Arg Asp Asn Gln Leu Val Val Pro Ser
Glu Gly Leu Tyr Leu Ile Tyr Ser Gln Val
Leu Phe Lys Gly Gln Gly Cys Pro Ser Thr
His Val Leu Leu Thr His Thr Ile Ser Arg
Ile Ala Val Ser Tyr Gln Thr Lys Val Asn
Leu Leu Ser Ala Ile Lys Ser Pro Cys Gln
Arg Glu Thr Pro Glu Gly Ala Glu Ala Lys
Pro Trp Tyr Glu Pro Ile Tyr Leu Gly Gly
Val Phe Gln Leu Glu Lys Gly Asp Arg Leu
Ser Ala Glu Ile Asn Arg Pro Asp Tyr Leu
Asp Phe Ala Glu Ser Gly Gln Val Tyr Phe
Gly Ile Ile Ala Leu.
```

27. The method of claim 24, wherein said polypeptide is administered by injecting a pharmaceutically acceptable, injectable solution of said polypeptide.

28. A process for preparing a polypeptide having human tumor necrosis factor activity which comprises:
cultivating a microorganism or cell culture transformed with a deoxyribonucleic acid comprising a base sequence capable of coding for a physiologically active human tumor necrosis factor polypeptide comprising an amino acid sequence represented by the following formula:

```
Ser Ser Ser Arg Thr Pro Ser Asp Lys Pro
Val Ala His Val Val Ala Asn Pro Gln Ala
Glu Gly Gln Leu Gln Trp Leu Asn Arg Arg
Ala Asn Ala Leu Leu Ala Asn Gly Val Glu
Leu Arg Asp Asn Gln
``` wherein Gln stands for a glutamine residue, Asp an aspartic acid residue, Pro a proline residue, Tyr a tyrosine residue, Val a valine residue, Lys a lysine residue, Glu a glutamic acid residue, Ala an alanine residue, Asn an asparagine residue, Leu a leucine residue, Phe a phenylalanine residue, Gly a glycine residue, His a histidine residue, Ser a serine residue, Thr a threonine residue, Ile an isoleucine residue, Trp a tryptophan residue, Arg an arginine residue, and Cys a cysteine residue, or a variant of said polypeptide having all of the activity of human tumor necrosis factor; and
recovering said polypeptide.

29. The process of claim 28, wherein said base sequence comprises at least one base sequence selected from the group consisting of a base sequence represented by the following formula and a base sequence complementary to said base sequence:

```
TCA TCT TCT CGA ACC CCG AGT GAC
                AAG CCT GTA GCC CAT GTT GTA
GCA AAC CCT CAA GCT GAG GGG CAG
                CTC CAG TGG CTG AAC CGC CGG
GCC AAT GCC CTC CTG GCC AAT GGC
                GTG GAG CTG AGA GAT AAC CAG
CTG GTG GTG CCA TCA GAG GGC CTG
                TAC CTC ATC TAC TCC CAG GTC
CTC TTC AAG GGC CAA GGC TGC CCC
                TCC ACC CAT GTG CTC CTC ACC
CAC ACC ATC AGC CGC ATC GCC GTC
                TCC TAC CAG ACC AAG GTC AAC
CTC CTC TCT GCC ATC AAG AGC CCC
                TGC CAG AGG GAG ACC CCA GAG
GGG GCT GAG GCC AAG CCC TGG TAT
                GAG CCC ATC TAT CTG GGA GGG
GTC TTC CAG CTG GAG AAG GGT GAC
                CGA CTC AGC GCT GAG ATC AAT
CGG CCC GAC TAT CTC GAC TTT GCC
                GAG TCT GGG CAG GTC TAC TTT
GGG ATC ATT GCC CTG
``` wherein A stands for a deoxyadenylic acid residue, G a deoxyguanylic acid residue, C a deoxycytidylic acid residue and T a thymidylic acid residue and wherein the left end and right end of said formula represent the 5'-hydroxyl group side and 3'-hydroxyl group side, respectively, or comprising a base sequence which is obtained by substituting at least one base of said base sequence in accordance with the degeneracy of the Genetic Code.

30. The process of claim 28, which comprises cultivating a microorganism transformed with a plasmid containing said base sequence in a culture medium, recovering said polypeptide from said microorganism or said culture medium and purifying said polypeptide.

31. The process of claim 30, wherein said microorganism is a bacterium.

32. The process of claim 31, wherein said bacterium is *Escherichia coli*.

33. The process of claim 32, wherein said *Escherichia coli* is *Escherichia coli* K-12.

34. The microorganism *E. coli* k-12 strain JM83 (pHGE).

35. The plasmid pHGE.

36. Isolated human genomic DNA which upon expression results in a human tumor necrosis factor polypeptide having an amino acid sequence represented by the following formula:

Ser Ser Ser Arg Thr Pro Ser Asp Lys Pro Val Ala His Val Val
Ala Asn Pro Gln Ala Glu Gly Gln Leu Gln Trp Leu Asn Arg
Arg Ala Asn Ala Leu Leu Ala Asn Gly Val Glu Leu Arg Asp
Asn Gln Leu Val Val Pro Ser Glu Gly Leu Tyr Leu Ile Tyr
Ser Gln Val Leu Phe Lys Gly Gln Gly Cys Pro Ser Thr His
Val Leu Leu Thr His Thr Ile Ser Arg Ile Ala Val Ser Tyr
Gln Thr Lys Val Asn Leu Leu Ser Ala Ile Lys Ser Pro Cys Gln
Arg Glu Thr Pro Glu Gly Ala Glu Ala Lys Pro Trp Tyr Glu
Pro Ile Tyr Leu Gly Gly Val Phe Gln Leu Glu Lys Gly Asp
Arg Leu Ser Ala Glu Ile Asn Arg Pro Asp Tyr Leu Asp Phe
Ala Glu Ser Gly Gln Val Tyr Phe Gly Ile Ile Ala Leu wherein Gln stands for a glutamine residue, Asp an aspartic acid residue, Pro a proline residue, Tyr a tyrosine residue, Val a valine residue, Lys a lysine residue, Glu a glutamic acid residue, Ala an alanine residue, Asn an asparagine residue, Leu a leucine residue, Phe a phenylalanine residue, Gly a glycine residue, His a histidine residue, Ser a serine residue, Thr a threonine residue, Ile an isoleucine residue, Trp a tryptophan residue, Arg an arginine residue, and Cys a cysteine residue.

37. A replicable recombinant DNA which comprises: a replicable vector; and the isolated human genomic DNA of claim 36.

38. The replicable recombinant DNA of claim 37, which is a plasmid.

39. A microorganism transformed with the replicable recombinant DNA of claim 38.

40. The microorganism of claim 39, which is *E. coli*.

* * * * *